United States Patent [19]

Kurth et al.

[11] Patent Number: 5,650,294
[45] Date of Patent: Jul. 22, 1997

[54] ISOLATED PROMOTER AND TERMINATOR OF ELONGATION FACTOR 1-α

[75] Inventors: Roland Kurth, Limburgerhof; Peter Philippsen; Sabine Steiner, both of Giessen; Martin C. Wright, Biberach an der Riss, all of Germany

[73] Assignee: BASF Aktiengesellschaft, Ludwigshafen, Germany

[21] Appl. No.: 329,681

[22] Filed: Oct. 26, 1994

Related U.S. Application Data

[63] Continuation of Ser. No. 941,140, Nov. 13, 1992, abandoned.

[30] Foreign Application Priority Data

Jun. 25, 1990 [DE] Germany .................. 40 20 181.3

[51] Int. Cl.$^6$ .............. C12P 21/06; C12N 1/15; C12N 15/11
[52] U.S. Cl. .............. 435/69.1; 435/71.1; 435/254.11; 536/24.1
[58] Field of Search .............. 435/69.1, 69.9, 435/71.1, 254.1, 254.11, 254.2, 255.1; 536/24.1

[56] References Cited

FOREIGN PATENT DOCUMENTS 34 20 310   5/1984   Germany .

OTHER PUBLICATIONS

Pokalsky et al (1989) Nuc. Acids. Res. 17, 4661–4673.
Bigelis in "Gene Manipulations in Fungi" (Bennet et al. Eds) Academic Press, Inc., Orlando Fla pp. 357–401 (1985).
Linz et al (1986) Mol. Cell. Biol. 6, 593–600.
Timberlake et al (1989) Science 244, 1313–1317.
Keller et al (1988) Biochemistry 27, 1117–1120.
Maniatis in "Molecular Cloning: A Laboratory Manual" Cold Spring Harbor Laboratory Press pp. 1.5, 1.6, 16.9, 16.10 & 16.12 (1989).
Woudt et al., Nucleic Acids Research, 1987, vol. 15(15): pp. 6037–6048.
*15th Int. Conf. on Yeast Genetics and Molecular Biology;* Steiner et al., 1990, "The gene for the translation elongation factor . . . ", Spec. Iss. 0244–01.
*Chem. Abst.;* Szczesniak et al., "Biosynthesis of Riboflavin"; 1973; 78(15), 350, No. 96073K.
*CRC Critical Reviews in Biotech.;* Rambosek et al., "Recombinent DNA in Filementors Fungi: Progress and Prospects"; 1987; vol. 6; 357–393.
Sundstrom et al (1990) J. Bacteriol. 172, 2036–2045.
Nagata et al (1984) EMBO J. 3, 1825–1830.
Schirmaier et al (1984) EMBO J. 3, 3311–3315.
Hovemann et al (1988) Nuc. Acids Res. 16, 3175–3194.

*Primary Examiner*—Mindy Fleisher
*Assistant Examiner*—Terry A. McKelvey
*Attorney, Agent, or Firm*—Keil & Weinkauf

[57] ABSTRACT

The promoter region of the *A. Gossypii* gene which encodes translation elongation factor EF-1α is described. The promoter can be employed for protein synthesis.

8 Claims, 16 Drawing Sheets

Mutations in the ATG region

```
Wild type         CGAACATAAACAAAAATGGGTAAGGAAAAG
                  GCTTGTATTTGTTTTTACCCATTCCTTTTC NcoI cleavage     CGAACATAAACAACCATGGGTAAGGAAAAG
site              GCTTGTATTTGTTGGTACCCATTCCTTTTC NsiT cleavage     CGAACATAAACAAAAATGCATAAGGAAAAG
site              GCTTGTATTTGTTTTTACGTATTCCTTTTC SphI cleavage     CGAACATAAACAAGCATGCGTAAGGAAAAG
site              GCTTGTATTTGTTCGTACGCATTCCTTTTC
```

New cleavage sites were introduced into the ATG region by substitution in the wild-type sequence by the underlined nucleotides.

Mutations in the terminator region:

```
Wild type         GGCTGGTAAGAAATAGAGTAACTGACAAT
                  CCGACCATTCTTTATCTCATTGACTGTTA ScaI cleavage     GGCTGGTAAGAAATAGAGT ACTGACAAT
site              CCGACCATTCTTTATCTCA TGACTGTTA
```

An ScaI cleavage site was introduced in the terminator region by deletion of an A/T base pair.

FIG. 17

```
AAGCTTGCCTCGTCCCCGCCGCGGGTCACCCGGCCAGCGACATGGAGGCC
HindIII

CAGATACCCTCCTTGACAGTCTTGACGTGCGCAGCTCACGGGGCATGATGT

GACTGTCGCCCGTACATTTAGCCCATACATCCCCATGTATAATCATTTGCA

TCCATACATTTTGATGGCCGCGACGGCGCGAAGCAAAAATTACGGCTCCTC

GCTGCAGACCTGCGAGCAGGGAAACGCTCCCCTCAGCAGACGCGTTGAATT
                                              ECORI

CTCCCCACGGCGCGCCCCTGTAGAGAAATATAAAGGTTAGGATTTGCCAC

TGAGGTTCTTCTTTCATATACTTCCTTTTAAAATCTTGCTAGGATACAGTT

Start
CTCACATCACATCCGAACATAAACAAAAATGGGTAAGGAAAAGACTCACGT
                                               HincII Stop
TGACCTGGAGGTCCCGCCCAAAAGGCTGGTAAGAAATAGAGTACTGACAA
    XhoI                                     ScaI

TAAAAAGATTCTTGTTTTCAAGAACTTGTCATTTGTATAGTTTTTTTATAT

TGTAGTTGTTCTATTTTAATCAATGTTAGCGTGATTTATATTTTTTTTGC

CTCGACATCATCTGCCCAGATGCGAAGTTAAGTGCGCAGAAAGTAATATCA

TGCGTCAATCGTATGTGAATGCTGGTCGCTATACTGCTGTCGATTCGATAC

TAACGCCGCCATCCAGTGTCT
```

FIG. 19

ISOLATED PROMOTER AND TERMINATOR OF ELONGATION FACTOR 1-α

This application is a continuation of application Ser. No. 07/941,140, filed on Nov. 13, 1992, now abandoned.

BACKGROUND OF THE INVENTION

The present invention relates to a promoter region from *Ashbya gossypii* (=*A. gossypii*), to fungi which have been genetically modified with this promoter region, and to the use thereof.

*A. gossypii* is employed for the production of vitamin $B_2$ by fermentation. It is desirable to extend the use of the fermentation technology available for *A. gossypii* by producing protein products using genetic engineering methods. An expression system for *A. gossypii* is required for this purpose. Systems of this type have already been described for some higher ascomycetes such as *Aspergillus niger* (Rambosek and Leach, CRC Critical Reviews in Biotechnology 6 (1987), 357–393). By contrast, to date no experience in the area of genetic engineering is available with the hemiascomycete *A. gossypii*, which is the sole representative of its genus.

An essential component of a system for the expression of genes which code for a required product is the so-called promoter region which is composed of 1) a functional promoter which is indispensable for transcription of the gene, and
2) the 5' non-coding region (between promoter and translation start) which is necessary for translation after transcription into mRNA.

SUMMARY OF THE INVENTION

The invention relates to the promoter region of the *A. gossypii* TEF gene which encodes translation elongation factor EF-1α (=TEF-1α).

This gene is very strongly expressed and therefore has a very efficient promoter region.

The promoter region obtained according to the invention has the nucleotide sequence indicated in SEQ ID NO:1. Since the limits of the functional regions of a novel and sequenced promoter region, which have the ability to initiate transcription and translation, can be defined well at the 3' end and less well at the 5' end, it cannot be ruled out that the natural promoter region of *A. gossypii* gene differs slightly in length from the indicated sequence.

The invention further relates to the terminator region of the *A. gossypii* TEF gene which encodes translation elongation factor EF-1α (=TEF-1α).

The terminator region can be used for efficient termination of transcription.

The terminator region obtained according to the invention has the nucleotide sequence indicated in SEQ ID NO:2, position 1513–2095. 3'-Terminal truncations of this sequence are also suitable as transcription terminator.

The terminator region can be used in conjunction with the TEF-promoter region or with other homologous or heterologous promoters.

The invention further relates to fungi which contain the abovementioned promoter region or parts thereof and/or the abovementioned terminator region or parts thereof.

The promoter region can be inserted, in particular, into the following fungi: *Ashbya gossypii*, species closely related to Ashbya, such as, in particular, *Eremothecium ashbyi* and genera unrelated to Ashbya, such as, in particular, Aspergillus and Neurospora.

The novel promoter region can be prepared a) by cloning the gene for translation elongation factor EF-1α (TEF gene) from *A. gossypii* including adjoining DNA sequences and subsequently cleaving, b) by fusion of *A. gossypii* DNA fragments to an open reading frame of a promoterless gene which is selectable in *A. gossypii*, isolation of strongly expressing transformants and subsequent selection of the TEF promoter, c) by chemical synthesis using known methods.

The novel promoter region makes it possible, together with suitable vector systems, to bring about overexpression of homologous and heterologous proteins in *A. gossypii* and other fungi. This may entail, for example, constitutively enhanced expression of genes of vitamin $B_2$ biosynthesis, and of genes which are responsible for overproduction of vitamin $B_2$, or the overexpression and isolation of proteins which are of economic importance. It is furthermore possible with the aid of the novel promoter region to utilize the post-transcriptional modification potential (e.g. glycosilation) of *A. gossypii*, which in some circumstances differs from that of other fungi. Since it is not possible to prepare all heterologous proteins in sufficient amounts by the systems hitherto used, such as Aspergillus or Saccharomyces, the development of expression systems with the efficient TEF promoter region for novel host organisms (for example *A. gossypii* in this case) is of great importance.

ori: origin for plasmid replication in *E. coli*; lacZ: *E. coli* lacZ gene; prom: 1500 bp *A. gossypii* DNA fragment with the TEF promoter region.

Figure 7:
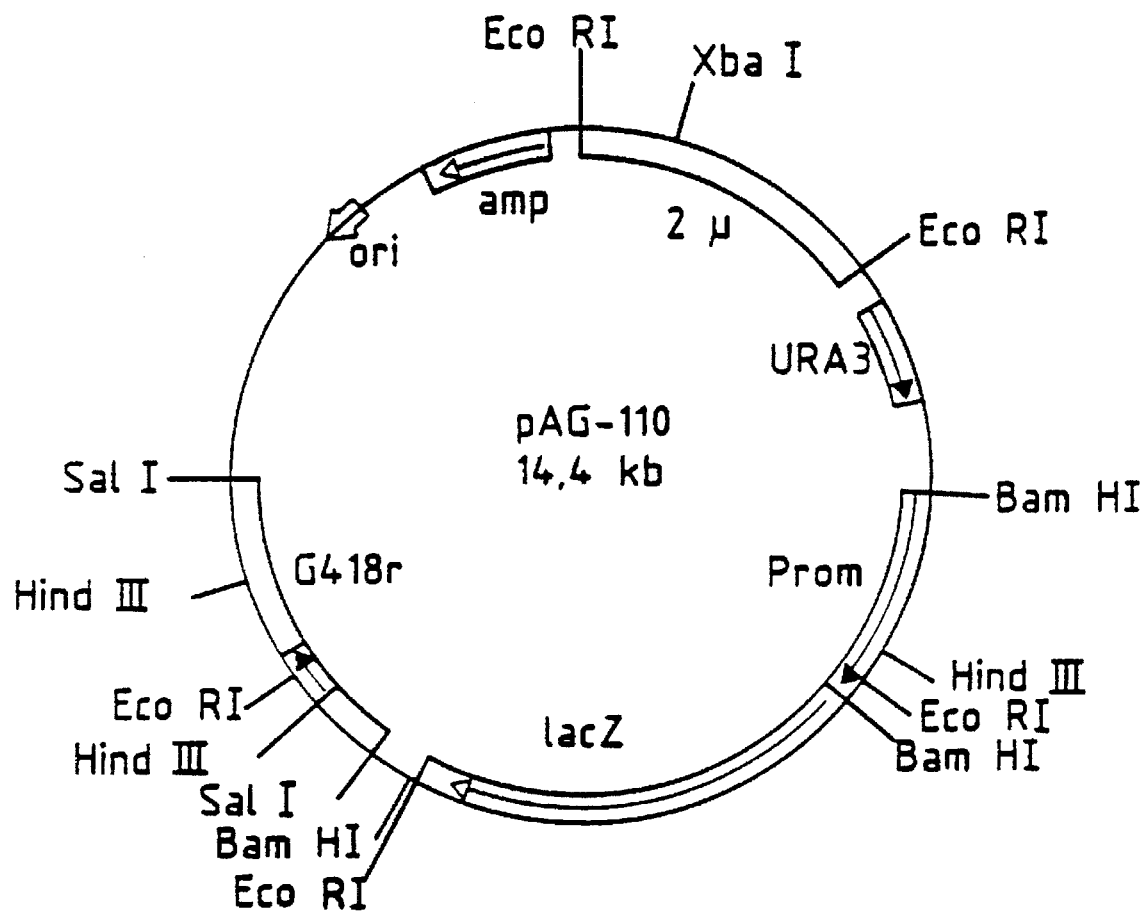

FIG. 7: Plasmid pAG-110. 2µ: EcoRI fragment of the *S. cerevisiae* 2µ plasmid with replication origin; URA3: *S. cerevisiae* URA3 gene; prom: 1500 bp *A. gossypii* DNA fragment with the TEP promoter region; lacZ; *E. coli* lacZ gene; G418r: G418 (kanamycin) resistance gene; ori: origin for plasmid replication in *E. coli*; amp: ampicillin-resistance gene; black arrow, 1500 bp *A. gossypii* DNA fragment with the TEF promoter region; white arrows represent the direction of transcription.

Figure 8:
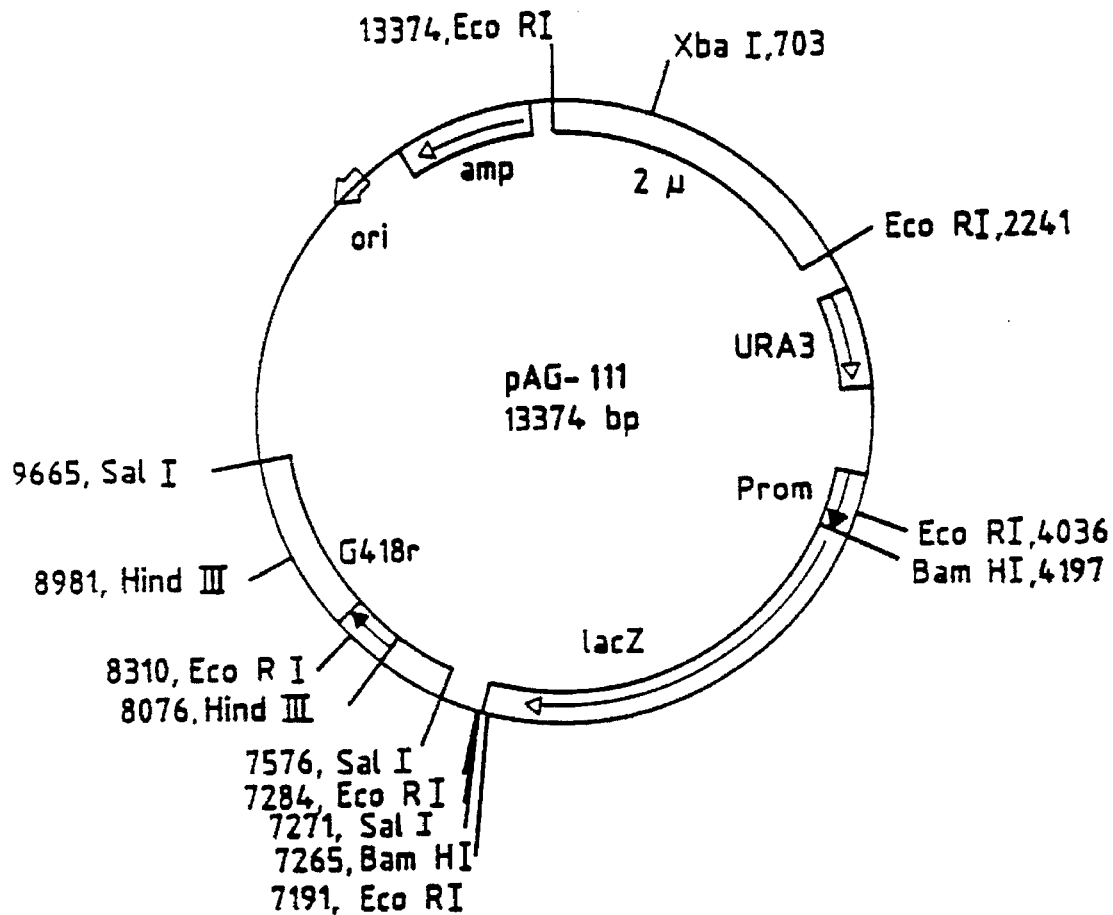

FIG. 8: Plasmid pAG-110. 2µ EcoRI fragment of the *S. cerevisiae* 2µ plasmid with replication origin; URA3: *S. cerevisiae* URA3 gene; prom, 403 bp *A. gossypii* DNA fragment with the TEF promoter region; lacZ: *E. coli* lacZ gene; G418r: G418 (kanamycin) resistance gene; ori: origin for plasmid replication in *E. coli*; amp: ampicillin-resistance gene; black arrow: *A. gossypii* DNA fragment with the TEF promoter region; white arrows represent the direction of transcription.

Figure 9:
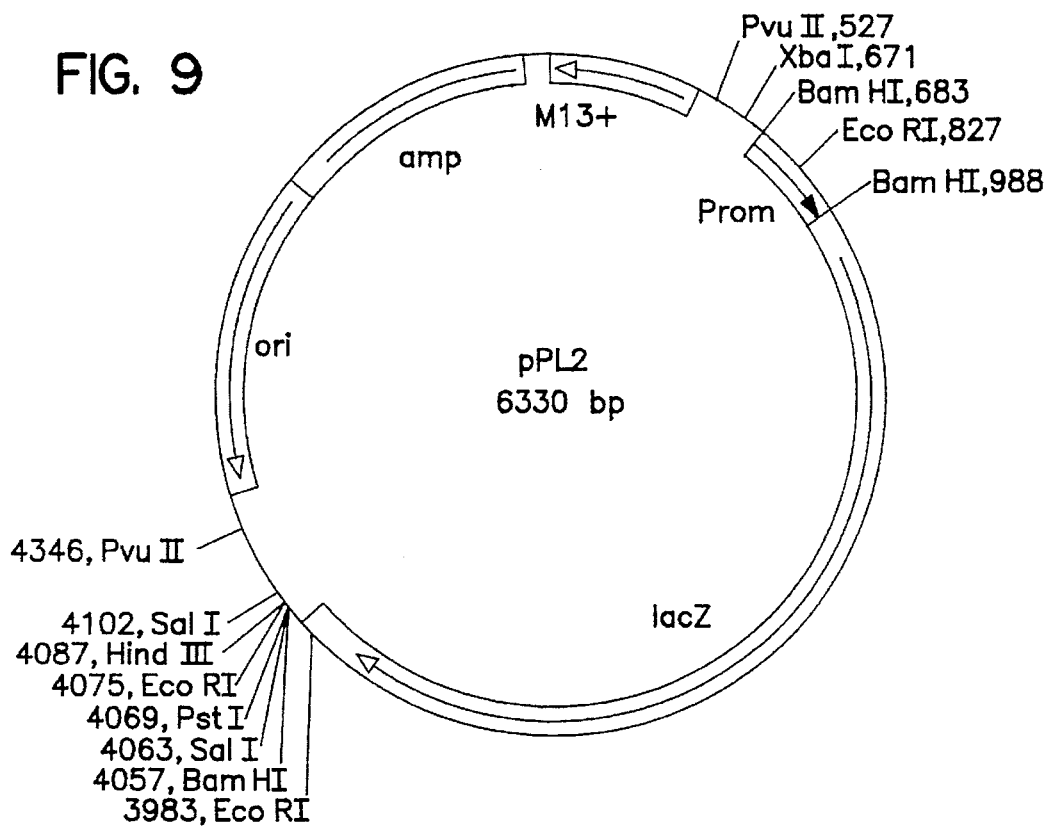

FIG. 9: Plasmid pPL2. amp: ampicillin-resistance gene; M13+: replication origin for single-stranded DNA isolation; ori: origin for plasmid replication in *E. coli*; lacZ; *E. coli* lacZ gene; prom: 294 bp *A. gossypii* DNA fragment with a part of the TEF promoter region (270 bp).

Figure 10:
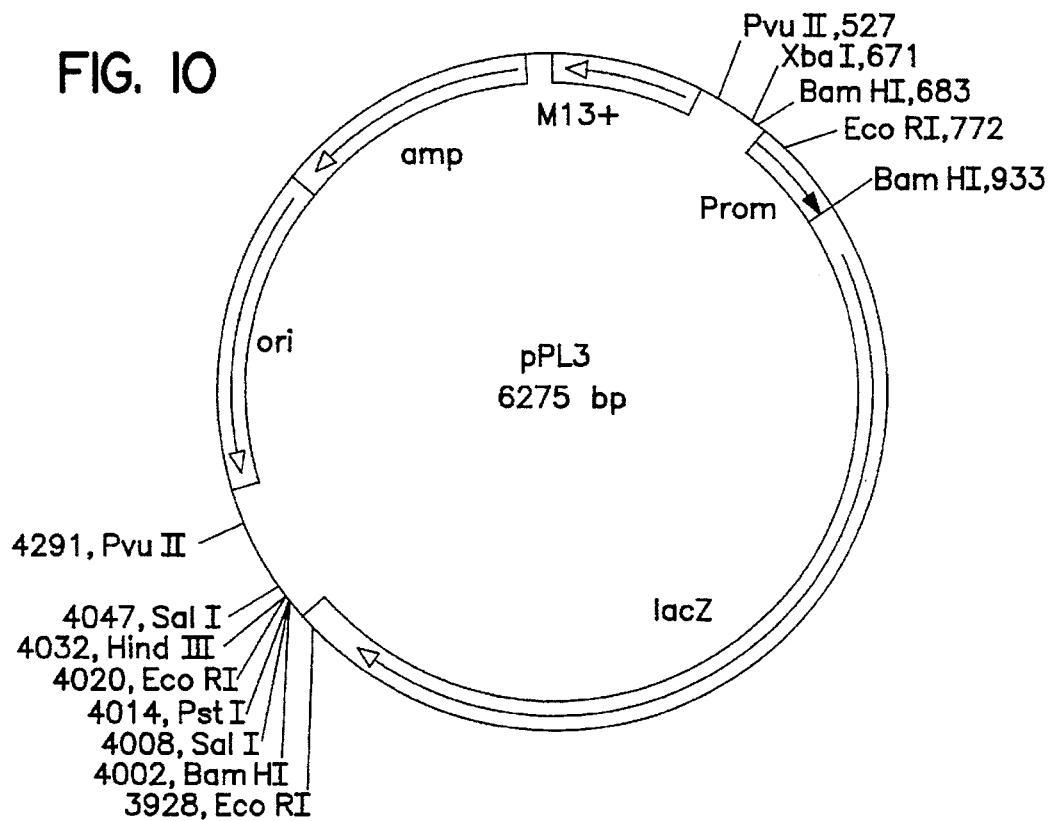

FIG. 10: Plasmid pPL3. amp: ampicillin-resistance gene; M13+: replication origin for single-stranded DNA isolation; ori: origin for plasmid replication in *E. coli*; lacZ; *E. coli* lacZ gene; prom: 239 bp *A. gossypii* DNA fragment with a part of the TEF promoter region (215 bp).

Figure 11:
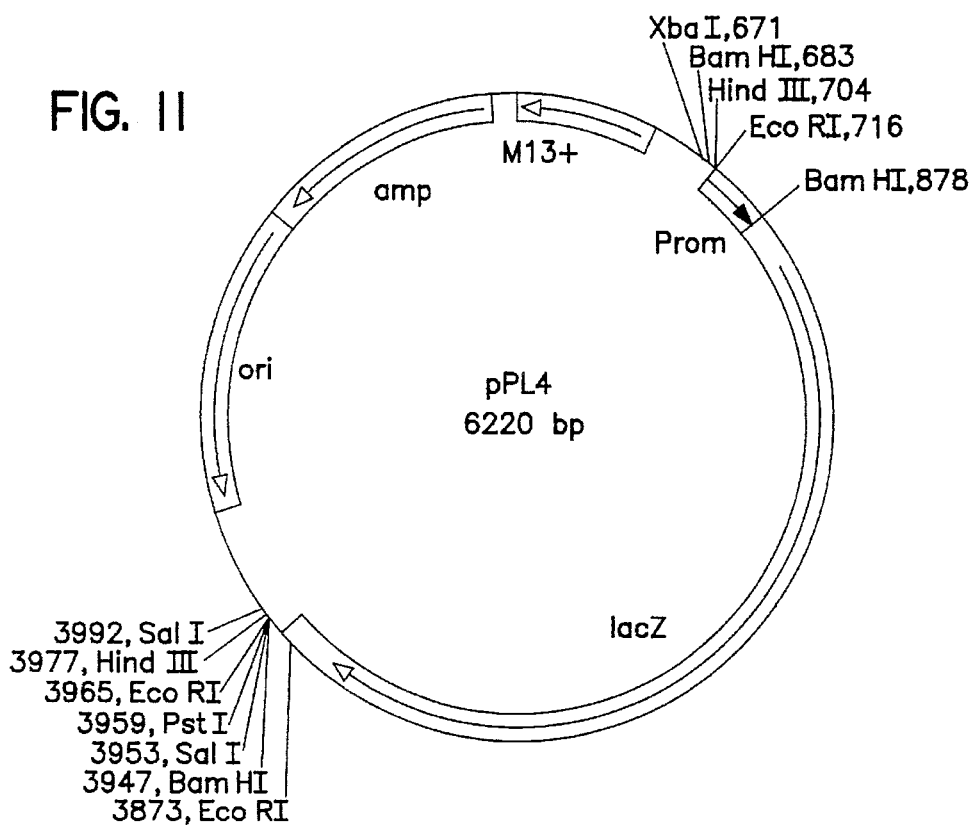

FIG. 11: Plasmid pPL4. amp: ampicillin-resistance gene; M13+: replication origin for single-stranded DNA isolation; ori: origin for plasmid replication in *E. coli*; lacZ; *E. coli* lace gene; prom; 158 bp *A. gossypii* DNA fragment with a part of the TEF promoter region (134 bp).

Figure 12:
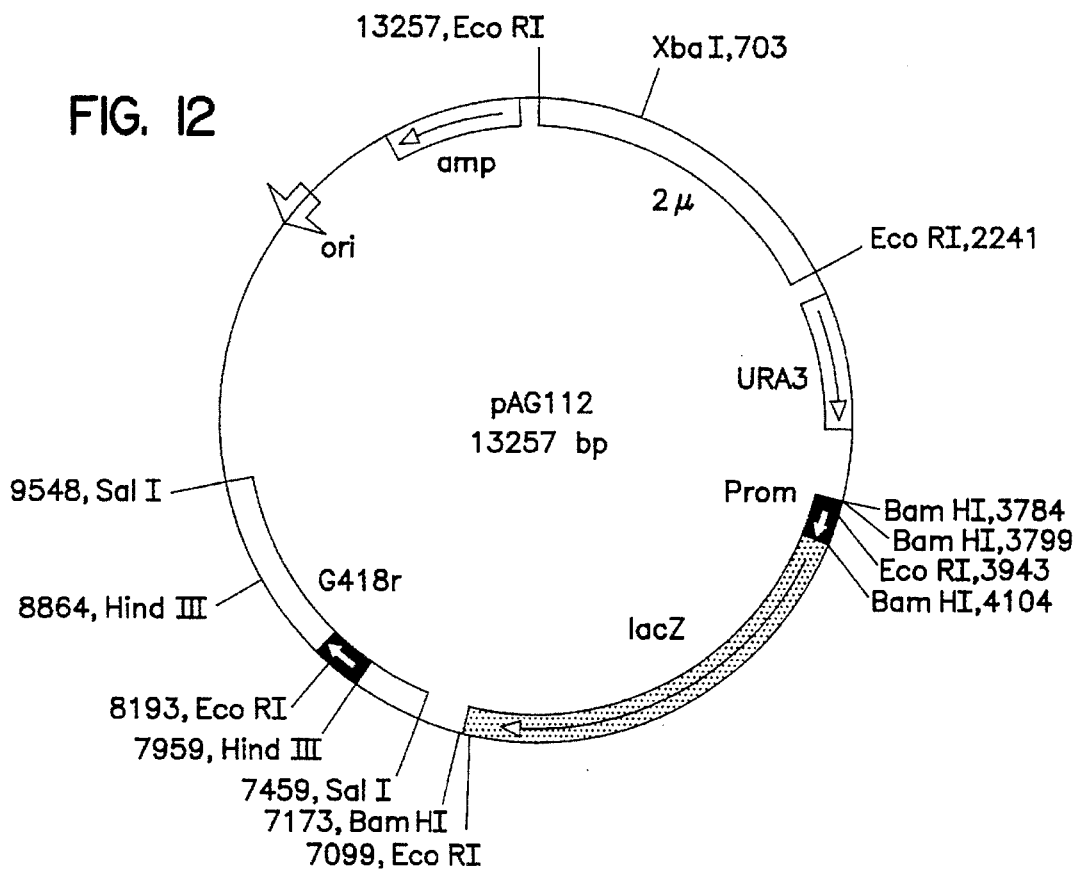

FIG. 12: Plasmid pAG-112. 2µ: EcoRI fragment of the *S. cerevisiae* 2µ plasmid with replication origin; URA3: *S. cerevisiae* URA3 gene; prom: 294 bp *A. gossypii* DNA fragment with the TEF promoter region; lacZ: *E. coli* lacZ gene; G418r: G418 (kanamycin) resistance gene; ori: origin for plasmid replication in *E. coli*; amp: ampicillin-resistance gene; black arrow: *A. gossypii* DNA fragment with the TEF promoter region; white arrows represent the direction of transcription.

Figure 13:
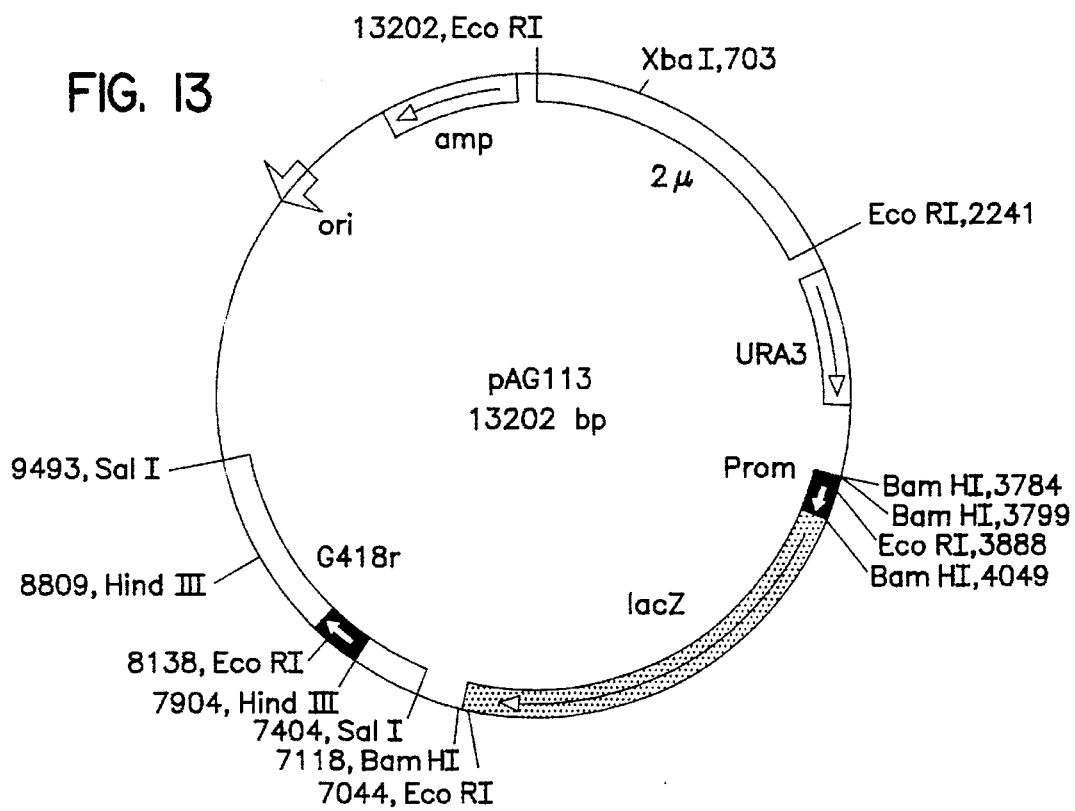

FIG. 13: Plasmid pAG-113, 2µ, EcoRI fragment of the *S. cerevisiae* 2µ plasmid with replication origin; URA3: *S. cerevisiae* URA3 gene; prom: 239 bp *A. gossypii* DNA fragment with the TEF promoter region; lacZ: *E. coli* lacZ gene; G418r: G418 (kanamycin) resistance gene) ori: origin for plasmid replication in *E. coli*; amp: ampicillin-resistance gene; black arrow: *A. gossypii* DNA fragment with the TEF promoter region; white arrows represent the direction of transcription.

Figure 14:
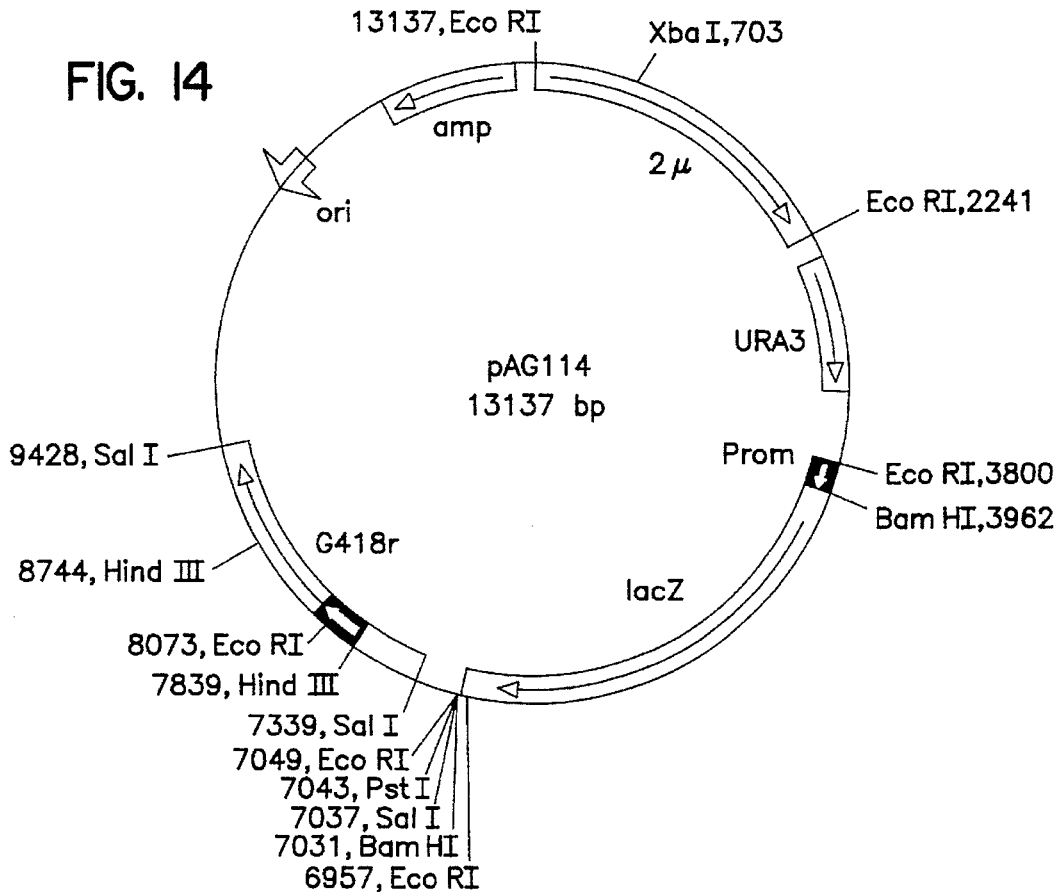

FIG. 14: Plasmid pAG-114, 2µ: EcoRI fragment of the *S. cerevisiae* 2µ plasmid with replication origin; URA3: *S. cerevisiae* URA3 gene; prom: 158 bp *A. gossypii* DNA fragment with the TEF promoter region; lacZ: *E. coli* lacZ gene; G418r: G418 (kanamycin) resistance gene; ori: origin for plasmid replication in *E. coli*; amp: ampicillin-resistance gene; black arrow: *A. gossypii* DNA fragment with the TEF promoter region; white arrows represent the direction of transcription.

Figure 15:
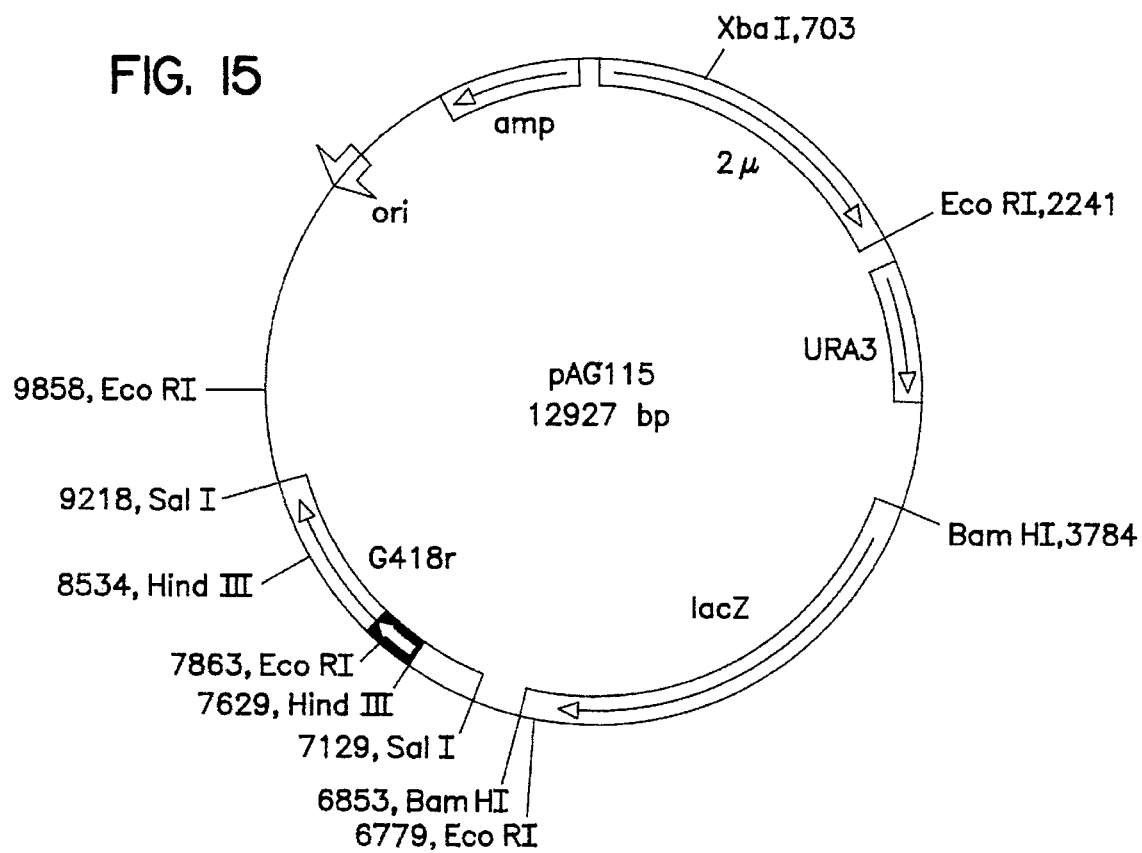

FIG. 15: Plasmid pAG-115. 2µ EcoRI fragment of the *S. cerevisiae* 2µ plasmid with replication origin; URA3: *S. cerevisiae* URA3 gene; lacZ: *E. coli* lacZ gene; G418r: G418 (kanamycin) resistance gene; ori: origin for plasmid replication in *E. coli*; amp: ampicillin-resistance gene; white arrows represent the direction of transcription.

Figure 16:
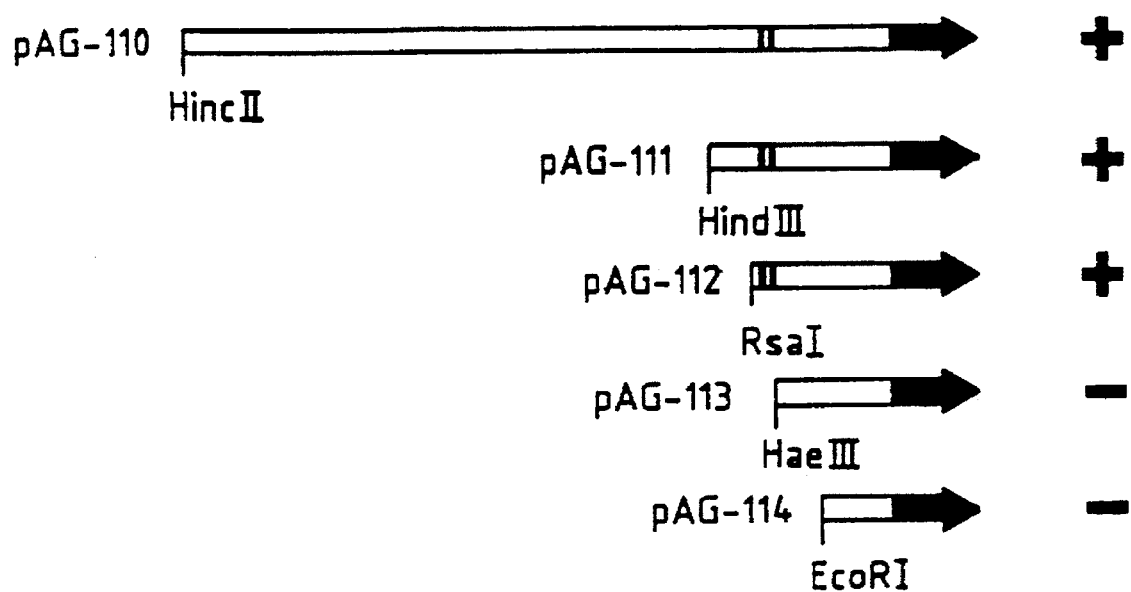

FIG. 16: TEF promoter fragments of the β-galactosidase expression plasmids.

FIG. 17: Nucleotide sequence in the ATG region and in the terminator region of M13PT1, M13PT2, M13PT3, pAG-201, pAG-202, pAG-203.

Mutations in the ATG region:

| Mutations in the ATG region: | |
|---|---|
| Wild Type: | Top strand (SEQ ID NO. 4) |
| | Bottom strand (SEQ ID NO. 5) |
| NcoI cleavage: | Top strand (SEQ ID NO. 6) |
| site | Bottom strand (SEQ ID NO. 7) |
| NsiT cleavage: | Top strand (SEQ ID NO. 8) |
| site | Bottom strand (SEQ ID NO. 9) |
| SphI cleavage: | Top strand (SEQ ID NO. 10) |
| site | Bottom strand (SEQ ID NO. 11) |
| Mutations in the terminator region: | |
| Wild Type: | Top strand (SEQ ID NO. 12) |
| | Bottom strand (SEQ ID NO. 13) |
| ScaI cleavage: | Top strand (SEQ ID NO. 15) |
| site | Bottom strand (SEQ ID NO. 16). |

Figure 18:
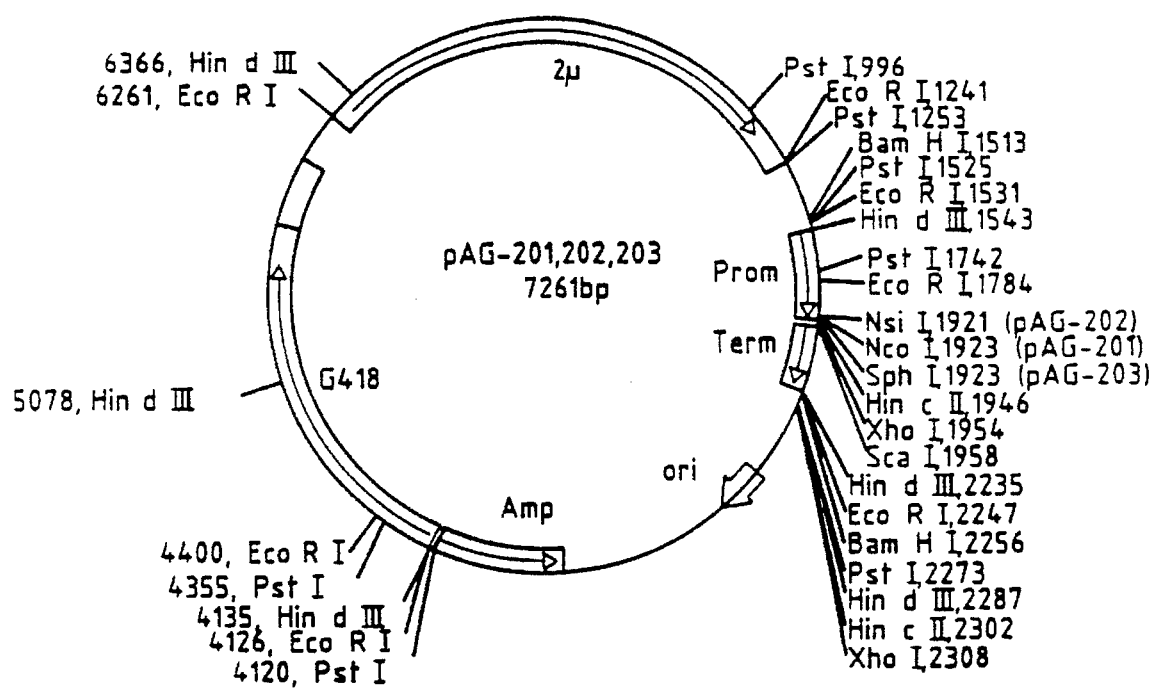

FIG. 18: Plasmid pAG-201, pAG-202, pAG-203. 2µ: ECORI fragment of the *S. cerevisiae* 2µ plasmid with replication origin, prom, term: 751 bp *A. gossypii* DNA fragment with the TEP promoter-terminator fusion. G418r:G418 (kanamycin) resistance gene; ori: origin point of plasmid replication in *E. coli*; amp: ampicillin-resistance gene; white arrows represent the direction of transcription.

FIG. 19: Nucleotide sequence of the fusion of the promoter and terminator of the TEF gene (SEQ ID NO:14).

DESCRIPTION OF THE PREFERRED EMBODIMENTS

1. Isolation of the *Ashbya gossypii* TEF gene

DNA isolated from *A. gossypii* mycelium was cut with the restriction endonucleases EcoRI and BamHI. DNA fragments which harbor the TEF gene or parts thereof were identified after separation of the restriction fragments according to size in an agarose gel electrophoresis and subsequent hybridization with a $^{32}$P-labeled heterologous TEF gene probe. The TEF gene probe comprises nucleotides 363 to 1235 of the 1377 bp-long open reading frame of the *S. cerevisiae* TEF2 gene (Schirmaier and Philippsen, EMBO J. 3 (1984), 3311–3315). A 4.6 kb-long EcoRI fragment and a 6.4 kb-long BamHI fragment hybridized with the heterologous TEF gene probe. Fragments with lengths in these ranges were eluted from from agarose gels, cloned into the vector pUC8 (Vieira and Messing, Gene 19 (1982), 259–268) which had been cut with EcoRI or BamHI, and transformed into *E. coli*. The clones with TEF DNA were identified by colony hybridization (Grunstein and Hogness, Proc. Natl. Acad. Sci. USA 72 (1975), 3961–3965) using the $^{32}$P-labeled heterologous probe. The positive clones contained either the 4.6 kb-long EcoRI fragment or the 6.4 kb-long BamHI fragment. The two clones overlap in a 2.1 kb region which carries the homology with the TEF gene probe and which was sequenced (SEQ ID NO:2). This 2.1 kb-long fragment contains the open reading frame of 1377 bp, 136 bp of the 5'-non-coding region and 582 bp of the 3'-non-coding region. Beyond the EcoRI cleavage site, a further 278 bp of the 5'-non-coding region were determined up to a HindIII cleavage site. Subsequently, the promoter region was isolated as 403 bp-long HindIII/HincII fragment which, besides the 379 bp in front of the start codon, also harbors the first 24 bp of the open reading frame of the TEF gene, and was employed for the constructions of pAG-100 and pAG-101 (SEQ ID NO:1).

Figure 1:
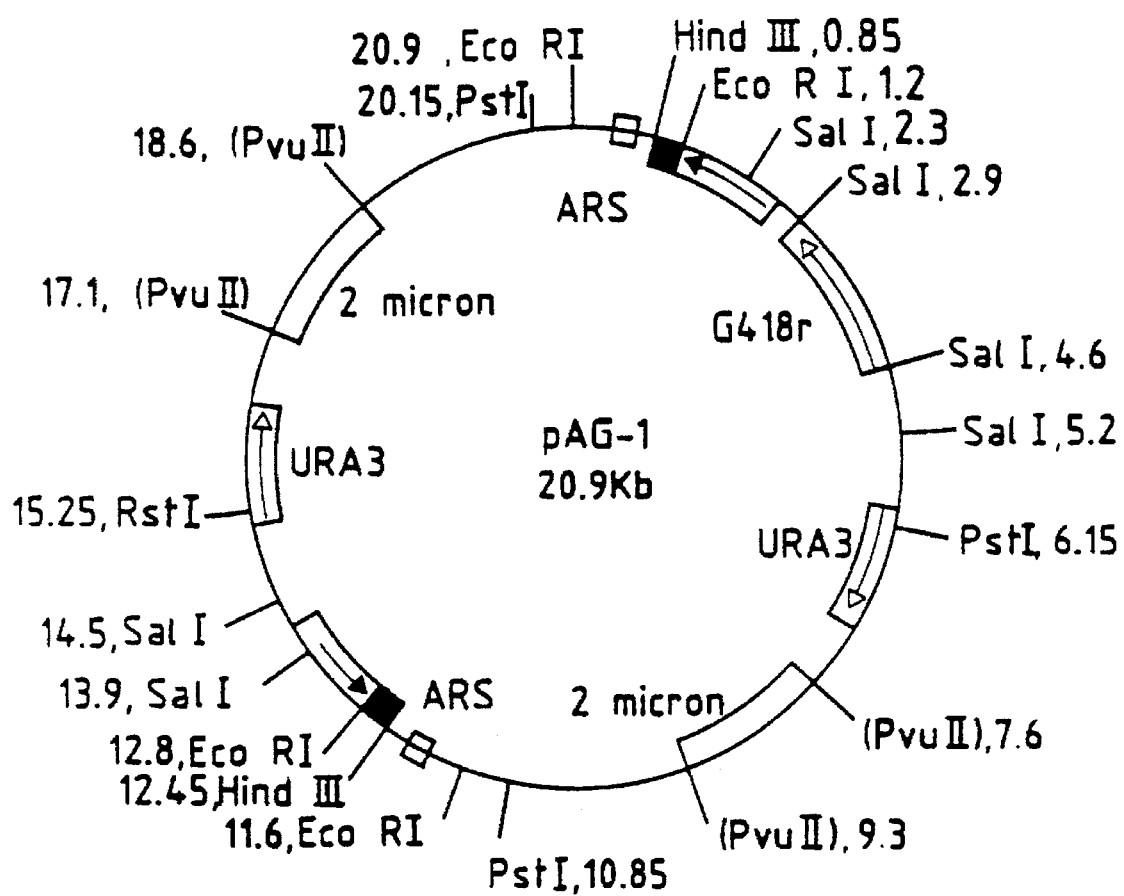
FIG. 1: Plasmid pAG-1. ARS: *S. cerevisiae* ARS1 sequence; 2 micron: EcoRI fragment of the *S. cerevisiae* 2μ plasmid with replication origin; URA3: *S. cerevisiae* URA3 gene; G418r: G418 (kanamycin) resistance; black arrow: *S. cerevisiae* cyc1-13 promoter; black box: *S. cerivisiae* CYC1 terminator; white arrows represent the direction of transcription.
Figure 2:
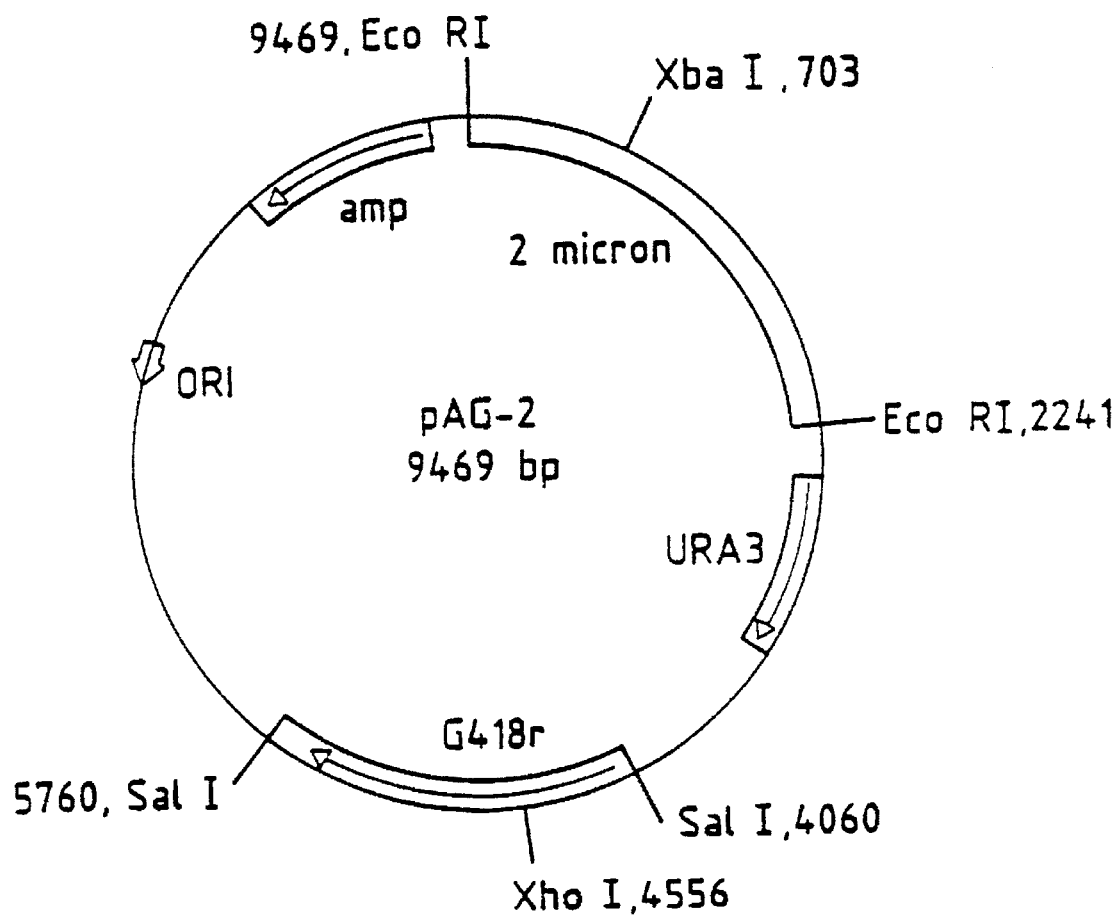
FIG. 2: Plasmid pAG-2. amp: ampicillin resistance; 2 micron: EcoRI fragment of the *S. cerevisiae* 2μ plasmids with replication origin; URA3: *S. cerevisiae* URA3 gene; G418r: G418 (kanamycin) resistance; ORI: origin of plasmid replication in *E. coli*; white arrows represent the direction of transcription.
Figure 3:
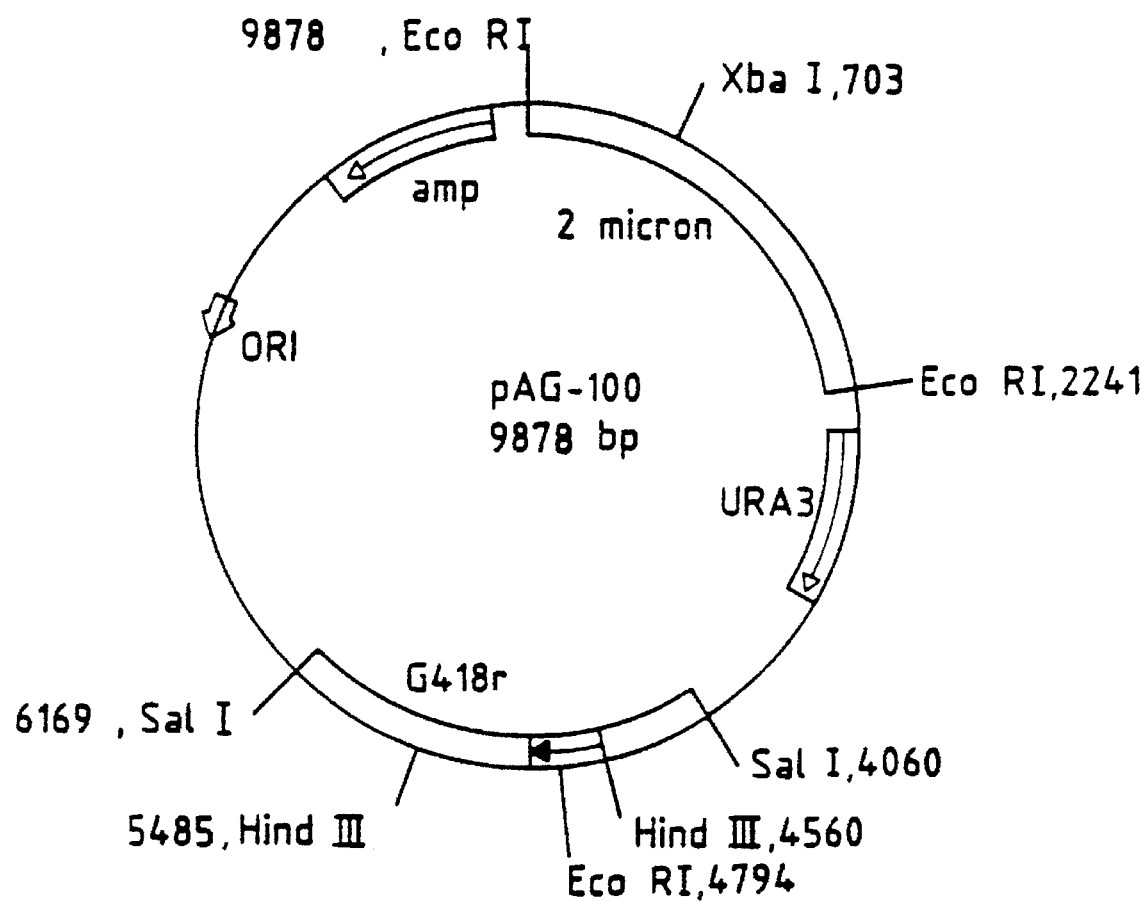
FIG. 3: Plasmid pAG-100. amp: ampicillin resistance; 2 micron: EcoRI fragment of the *S. cerevisiae* 2μ plasmid with replication origin; URA3: *S. cerevisiae* URA3 gene; G418r: G418 (kanamycin) resistance; ORI: origin of plasmid replication in *E. coli;* black arrow, *A. gossypii* DNA fragment with TEF promoter region; white arrows represent the direction of transcription.
Figure 4:
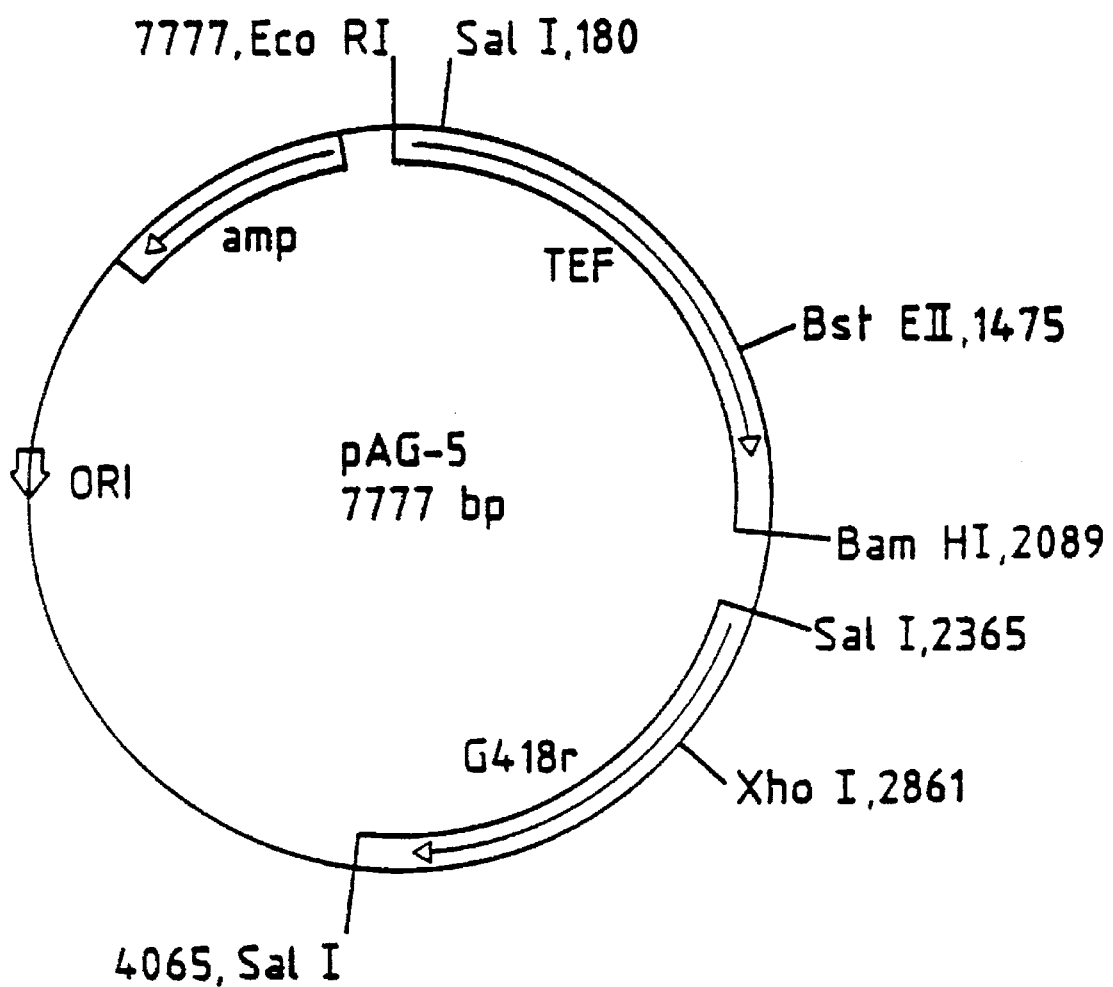
FIG. 4: Plasmid pAG-5. amp: ampicillin resistance; G418r: (kanamycin) resistance; ORI: origin of plasmid replication in *E. coli;* TEF: *A. gossypii* EcoRI/BamHI fragment with ORF for the translation elongation factor; white arrows represent the direction of transcription.
Figure 5:
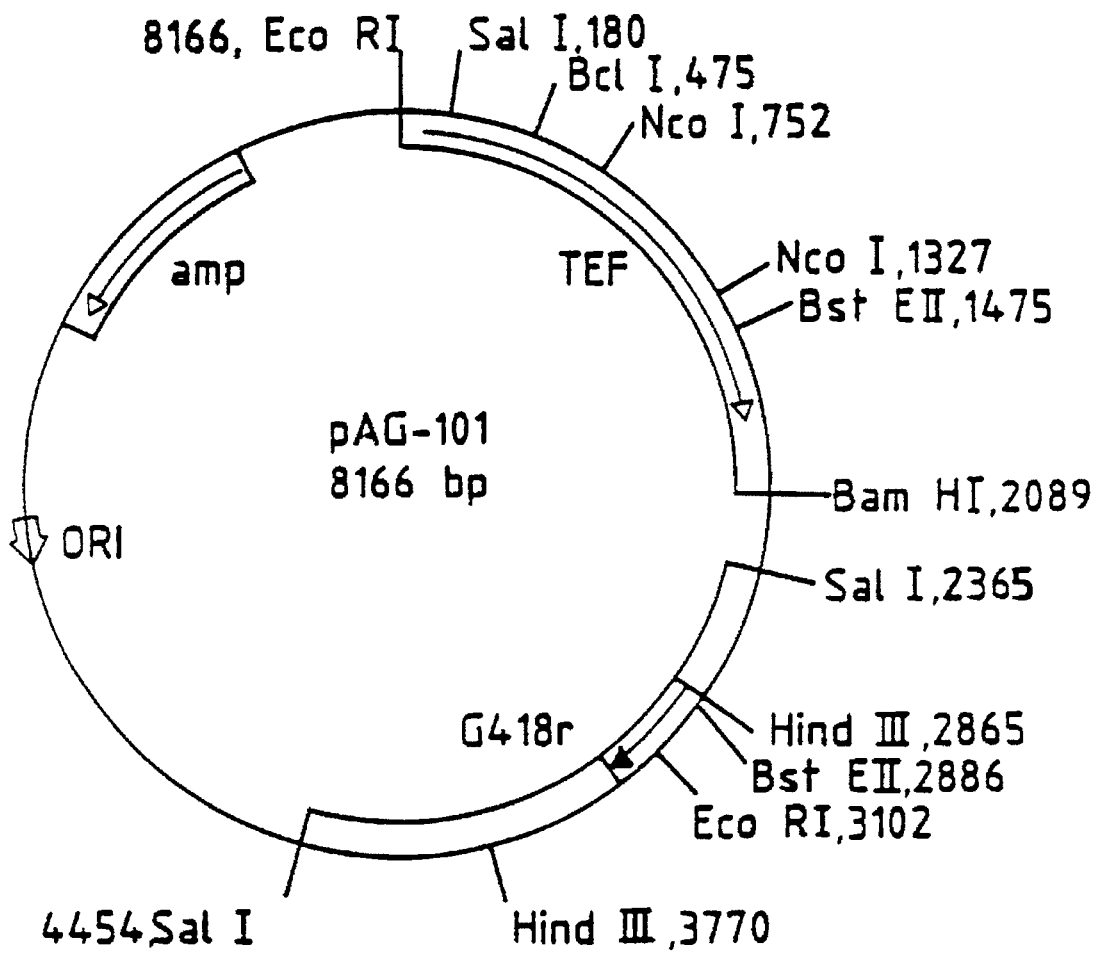
FIG. 5: Plasmid pAG-101. amp: ampicillin resistance; G418r: G418 (kanamycin) resistance; ORI: origin of plasmid replication in *E. coli;* TEF: *A. gossypii* EcoRI/BamHI fragment with ORF for the translation elongation factor; black arrow: *A. gossypii* DNA fragment with TEF promoter region; white arrows represent the direction of transcription.
Figure 6:
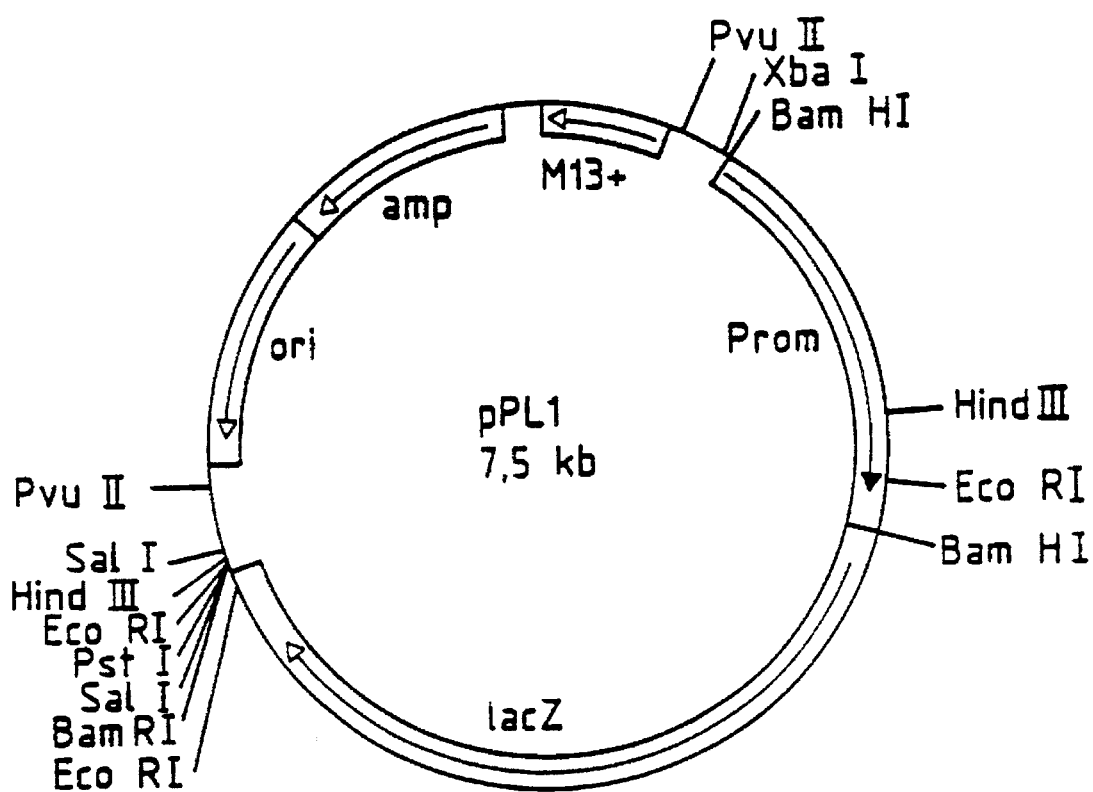
FIG. 6: Plasmid pPL1. amp: ampicillin-resistance gene; M13+: replication origin for single-stranded DNA isolation.

2. Plasmid constructions a) The vector pAG-1 (FIG. 1) (deposited DSM 6010), a derivative of the vector pEX4, was prepared as described by Ernst and Chan, J. Bacteriol. 163 (1985), 8–14. pAG-1 contains a 1.7 kb SalI fragment with the kanamycin-resistance gene, which codes for the aminoglycoside phosphotransferase (APH(3')I), of the transposon Tn903. In the original pEX4 construct, initially the 1695 bp PvuII fragment of Tn903 (Oka et al., J. Mol. Biol. 147 (1981), 217–226) was ligated into a plasmid with filled-in SalI cleavage sites. The SalI cleavage sites were retained in this way, and the resistance gene can be isolated as 1.7 kb SalI fragment. pAG-1 contains the *Saccharomyces cerevisiae* ARS elements ARS1 and 2μ ARS and undergoes autonomous replication in *Ashbya gossypii*.

b) pAG-2 (FIG. 2). The 1.7 kb SalI fragment with the kanamycin-resistance gene was cut out of pAG-1 and inserted into the SalI cleavage site of the *S. cerevisiae E. coli* shuttle vector XEp24 (Botstein et al., Gene 8 (1979), 17–24; New England Biolabs Inc., Beverly, Mass., U.S.A., 1988–1989 Catalog, 112–113). The structure of the newly produced plasmid—pAG-2—was checked by restriction endonuclease mapping, using the XhoI cleavage site which is located in the 1.7 kb SalI fragment to check the orientation of the insert. pAG-2 contains the *Saccharomyces cerevisiae* ARS element 2μ ARS and undergoes autonomous replication in *Ashbya gossypii*.

c) pAG-100 (FIG. 3). A 403 bp-long HindIII/HincII fragment which contains the promoter region and the first 24 bp of the open reading frame of the gene for translation elongation factor EF-1α (TEF gene) from *A. gossypii* was inserted, after the protruding ends had been filled in, into the XhoI cleavage site of pAG-2 which is located 30 bp in the 3' direction behind the translation start of the kanamycin-resistance gene. The orientation of the fragment in the plasmid pAG-100 produced in this way was checked by restriction endonuclease mapping with HindIII. Insertion of the 403 bp-long fragment resulted in replacement of the 10 N-terminal amino acids of APH(3')I by the first 8 amino acids of *A. gossypii* translation elongation factor EF-1α. Deletion or replacement of the first 19 amino acids of APH(3')I by other amino acids does not result in loss of activity (Chen and Fukuhara, Gene 69 (1988), 181–192). The sequence of the SalI fragment after insertion of the TEF promoter region is shown in SEQ ID NO:2. pAG-100 contains the *Saccharomyces cerevisiae* ARS element 2μ ARS and undergoes autonomous replication in *Ashbya gossypii*.

d) pAG-5 (FIG. 4). The 1.7 kb fragment with the kanamycin-resistance gene from pAG-1 was subcloned into the SalI cleavage site of pBR322 (Bolivar et al., Gene 2 (1977), 95–113). The resulting plasmid—pJL3A—contains in the pBR322 portion one BamHI cleavage site and one EcoRI cleavage site so that pJL3A is decomposed by double digestion into a 375 bp and a 5688 bp fragment. The large fragment was ligated to a 2.1 kb EcoRI/BamHI *A. gossypii* fragment which contains the open reading frame of the gene for translation elongation factor EF-1α (TEF gene) (sequence No. 1). The resulting plasmid was called pAG-5. pAG-5 contains no *Saccharomyces cerevisiae* ARS elements.

e) pAG-101 (FIG. 5). The 403 bp HindIII/HincII fragment with the promoter region and the first 24 bp of the open reading frame of the TEF gene from *A. gossypii* was inserted into the XhoI cleavage site located in the open reading frame of the kanamycin-resistance gene, as described for the construction of pAG-100. The plasmid produced in this way was called pAG-101. pAG-101 contains no *Saccharomyces cerevisiae* ARS elements. The sequence of the kanamycin-resistance gene-TEF promoter region fusion is set forth as SEQ ID NO:3.

f) pBKS1871 (precursor plasmid for TEF promoter-lacZ fusion): A 3113 bp-long PstI fragment from the plasmid pMC1871 (Shapira et al., Gene, 25 (1983), 71–82) was cloned into the PstI cleavage site of the plasmid pBKS$^+$ (Short et al., Nucleic Acid Res., 16 (1988), 7583–7600). The fragment harbors the open reading frame of the lacZ gene from *E. coli* (Kalnins et al., EMBO J., 2 (1983), 593–597) which lacks the first seven codons.

g) pPL1 (FIG. 6). pBKS1871 was linearized at the SmaI cleavage site in front of the lacZ gene. A 1500 bp HincII fragment which harbors the TEF promoter and adjoining sequences including the first eight codons of the TEF gene from *A. gossypii* was cloned into the linearized plasmid. This resulted in an open reading frame which codes for a β-galactosidase whose first seven amino acids are replaced by the first eight amino acids of the EF-1α from *A. gossypii*. It was possible to isolate TEF promoter-lacZ fusions with regions of various lengths of the TEF promoter from this plasmid.

h) pPL2 (FIG. 9). pBKS1871 was linearized at the SmaI cleavage site in front of the lacZ gene. A 294 bp-long RsaI/HincII fragment which contains parts of the TEF promoter (270 bp) and the first eight codons of the TEF gene from *A. gossypii* (24 bp) was cloned into the linearized plasmid.

i) pPL3 (FIG. 10). pBKS1871 was linearized at the SmaI cleavage site in front of the lacZ gene. A 239 bp-long HaeIII/HincII fragment which contains the first eight codons of the TEF gene (24 bp) and 215 bp of the regions, located in the 5' direction in front of the start codon, of the non-translated region was cloned into the linearized plasmid.

j) pPL4 (FIG. 11). pBKS1871 was linearized at the SmaI cleavage site in front of the lacZ gene. A 158 bp-long EcoRI/HincII fragment which contains the first eight codons of the TEF gene and 134 bp of the regions, located in the 5' direction in front of the start codon, of the non-translated region was cloned into the linearized plasmid.

k) pAG-110 (FIG. 7). Cleavage of pPL1 with XbaI and SalI resulted in isolation of a 4600 bp fragment which harbors the fusion of the 1500 bp-long TEF promoter fragment with the lacZ gene. After the protruding ends had been filled in, this fragment was cloned into the filled-in BamHI cleavage site of pAG-100.

l) pAG-111 (FIG. 8). Cleavage of pPL1 with HindIII resulted in isolation of a 3509 bp-long fragment. The TEF promoter region is truncated by 1100 bp in this fragment. It thus corresponds to the promoter region which in pAG-100, pAG-101, pAG-110 and pAG-111 controls transcription of the G418 resistance gene. After the protruding ends had been filled in, the 3509 bp-long fragment was cloned into the filled-in BamHI cleavage site of pAG-100.

m) pAG-112 (FIG. 12). After cleavage of pPL2 with XbaI and SalI, a 3392 bp-long fragment which harbors the fusion of the 294 bp-long promoter fragment with the lacZ gene was isolated and, after the protruding ends had been filled in, was inserted into the filled-in BamHI cleavage site of the plasmid pAG-100.

n) pAG-113 (FIG. 13). After cleavage of pPL3 with XbaI and SalI, a 3337 bp-long fragment which harbors the fusion of the 239 bp-long promoter fragment with the lacZ gene was isolated and, after the protruding ends had been filled in, was inserted into the filled-in BamHI cleavage site of the plasmid pAG-100.

o) pAG-114 (FIG. 14). After cleavage of pPL4 with HindIII, a 3273 bp-long fragment which harbors the fusion of the 158 bp-long promoter fragment with the lacZ gene was isolated and, after the protruding ends had been filled in, was inserted into the filled-in BamHI cleavage site of the plasmid pAG-100.

p) pAG-115 (FIG. 15). After cleavage of pBKS 1871 with BamHI, a 3069 bp-long fragment which harbors the open reading frame of the lacZ gene with the first seven codons of the open reading frame being missing and no promoter fragment being fused in front of the open reading frame was isolated. This fragment was inserted into the BamHI cleavage site of the plasmid pAG-100.

q) pAG-120.pBIIKS⁻ (Short et al., Nucleic Acid Res. 16 (1988), 7583–7600) was cleaved with SspI and ScaI, and a 2084 bp-long fragment was isolated. YEP24 (Botstein et al., Gene 8 (1979), 17–24) was cleaved with ScaI and ClaI, and a fragment 2782 bp in size was isolated. This was ligated, after the protruding ends had been filled in, to the 2084 bp-long ScaI/SspI fragment from pBIIKS⁻ so that a complete ampicillin-resistance gene was produced again (in pBIIKS⁻ and YEP24, ScaI cuts in the ampicillin-resistance gene).

r) pAG-121.pAG-100 was cut with SalI and HindIII, and a 669 bp-long fragment which harbors part of the G418-resistance gene was isolated. This was cloned into the SalI/HindIII cut plasmid pBIISK⁺ (Short et al., Nucleic Acid Res. 16 (1988), 7583–7600).

s) pAG-122.pAG-100 was cut with HindIII, and a 940 bp-long fragment which harbors part of the G418-resistance gene under the control of the TEF promoter. This was inserted into the HindIII-cut plasmid pAG-121 in such a way that a complete G418-resistance gene was produced. Transformation of this plasmid into *E. coli* permits transformant selection on kanamycin-containing medium.

t) pAG-123.pAG-122 was cut with SalI and BamHI, and a 1639 bp-long fragment which harbors the G418-resistance gene under the control of the TEF promoter was isolated. This was inserted into the ScaI-cut plasmid pAG-120, which made selection of *E. coli* transformants on kanamycin-containing medium possible.

u) pAG-130.pBIIKS⁺ (Short et al., Nucleic Acid. Res. 16 (1988), 7583–7600) was cleaved with HindIII and HincII, and the 403 bp-long HindIII/HincII TEF promoter fragment was inserted.

v) pAG-131. An HaeIII/AccI fragment which is 260 bp in size and which contains 25 nucleotides of the 3' end of the TEF gene and regions adjacent thereto in the 3' direction (terminator fragment) was isolated from the clone which harbors the fragment 2.1 kb in size, which contains the TEF gene, of genomic *A. gossypii* DNA. After the protruding ends had been filled in, this fragment was inserted into the plasmid pBIIKS⁻ which had been cleaved with HincII (Short et al., Nucleic Acid Res. 16 (1988), 7583–7600).

w) pAG-132. pag-130 was cut with ScaI and XhoI, and a fragment 2248 bp in size was isolated. pAG-131 was likewise cleaved with ScaI and XhoI, and a fragment 1442 bp in size was isolated and was ligated to the 2248 bp fragment from pAG-103 in such a way that a complete ampicillin-resistance gene was produced anew.

x) M13PT. pAG-132 was cleaved with BamHI, and a fragment which is 752 bp in size and which contains the fusion of TEF promoter fragment and TEF terminator fragment was isolated. This was cloned into the BamHI cleavage site of M13mp9.

y) M13PT1, M13PT2, M13PT3. M13PT was modified by oligonucleotide-directed mutagenesis (Kramer et al., Nucl. Acid. Res. 24 (1984), 9441–9556) so as to produce an ScaI cleavage site behind the stop codon of the TEF gene (in the terminator fragment) and an NcoI cleavage site (M13PT1), an NsiI cleavage site (M13PT2) or an SphI cleavage site (M13PT3) in the start codon of the TEF gene (in the promoter fragment) (FIG. 17).

z) pAG-201. pAG-202, pAG-203 (FIG. 18). M13PT1, M13PT2 and M13PT3 were cleaved with BamHI, and the fragment which is 751 bp in size and has promoter region and terminator region of the TEF gene was isolated from the cleavage. This TEF signal sequence was inserted into the BamHI cleavage site of the plasmid pAG-123 to yield the plasmid pAG-201. The same method was used to construct the plasmid pAG-202 from M13PT2 and the plasmid pAG-203 from M13PT3.

3. Transformation of *A. gossypii* with TEF Promoter Region Plasmids

The transformations were carried out in accordance with the following scheme:

Inoculate 200 ml of MA2 with about 1–2×10⁷ spores

Incubate in flasks with baffles at 27° C. and 350 rpm for 32–40 h.

Remove mycelium by filtration with suction and wash 1x in 30 ml of H₂O

Determine fresh weight (about 2–3 g)

Suspend mycelium in 30 ml of SD and incubate at 30° C. in a shaker for 30 min.

Suspend mycelium in 5–10 ml of SPEZ per g fresh weight

Incubate in a water bath shaker at 30° C., check protoplast formation under the microscope (a degree of protoplast formation of more than 90% should be reached after 30 min.)

Filter) protoplast suspension through glass filter (Schott, porosity 1)

Centrifuge filtrate for 5 min. (Sorvall SM24 rotor, 1800 rpm)

Wash sediment 1x in 20 ml of ST and 1x in 20 ml of STC

Suspend protoplasts in 20 ml of STC and determine titer in a counter

After centrifugation, resuspend protoplasts to a density of 4×10⁸/ml in STC

Add 100 μl of protoplast suspension to DNA in a maximum of 15 μl of TE and mix (amounts of DNA: for replicating TEF promoter region plasmids: 1–10 μg; for integrative transformation with linearized TEF promoter region plasmids: 15–20 μg)

Incubate at room temperature for 15 min.

Cautiously add 1 ml of PTC40 and mix by inversion

Centrifuge for 5 min. (Heraeus Biofuge A, 1500 rpm)

Cautiously remove supernatant, and suspend sediment in 1 ml of SMTCI

Incubate at 27° C. for 3 h., mix about every 45 min. by inversion

After centrifugation, suspend sediments in 1 ml of SM

Mix suspension with 9 ml of SMA2 top layer and place on SMA2 plate (20 ml of SMA2 agar per plate)

Incubate plates at 27° C. for 18 h.

Place G418 layer on plates (0.54 ml of G418 stock solution +0.46 ml of $H_2O$+6 ml of 0.5% of agarose (in $H_2O$, preheated to 42° C.))

Incubate plates further at 27° C., transformants are visible after 2–3 days in the case of replicating plasmids, and after 3–6 days in the case of integration Media and solutions

| Media: MA2: | Peptone (Gibco casein hydrolyzate (No. 140) | 10 g/l |
| --- | --- | --- |
| | Yeast extract (Gibco) | 1 g/l |
| | Glucose | 10 g/l |
| | myo-Inositol | 0.3 g/l |
| SMA2-agar: | Sorbitol | 1 M |
| | Peptone | 10 g/l |
| | Yeast extract | 1 g/l |
| | Glucose | 20 g/l |
| | myo-Inositol | 0.3 g/l |
| | Agar (Gibco) | 12 g/l |

SMA2 top layer: As SMA2 agar, 0.8% agarose in place of agar

Solutions:

SD: 1M sorbitol; 50 mM dithiothreitol

SPEZ: 1M sorbitol; 10 mM Na phosphate buffer pH 5.8; 10 mM EDTA; 2 mg/ml Zymolyase 20 T (Seikagaku Kogyo Co., Tokyo)

ST: 1M sorbitol; 10 mM tris-Cl pH 8

STC: 1M sorbitol; 10 mM tris-Cl pH 8; 10 mM $CaCl_2$

TE: 10 mM tris-Cl; 1 mM EDTA

PTC40: 40% (w/v) polyethylene glycol 4000 (Merck); 10 mM tris-Cl pH 8; 10 mM $CaCl_2$ SMTCI: 50% SM (see below); 50% STC; 0.03 g/l myo-inositol SM: 50% 2M sorbitol; 50% MA2

G418 stock solution: 20 mg/ml G 418 (Geneticin, Gibco) in $H_2O$

4. Results of Transformation with TEF Promoter Region Plasmids

The results of various transformations carried out as in Example 3 are compiled in Table 1. In all the experiments, transformants were selected with a G418 concentration of 0.3 mg/ml per transformation plate. Growth of *A. gossypii* mycelium is completely inhibited at this G418 concentration. On transformation with the recombinant DNA vectors pAG-1 and pAG-2, in which the G418-resistance gene is under the control of the original bacterial promoter and not under the control of the TEF promoter region, no transformants are produced at this concentration. In order to obtain transformants with these recombinant DNA vectors, the G418 concentration must not exceed 0.1 mg/ml per transformation plate. At this concentration up to 80% of the colonies which appear are not transformants.

TABLE 1

Transformation results

| Experiment | Plasmid | DNA per transf., µg | Transformants per µg of DNA | Transformants per viable protoplasts |
| --- | --- | --- | --- | --- |
| 1 | pAG-1 | 10 | 0 | 0 |
| 1 | pAG-2 | 10 | 0 | 0 |
| 1 | pAG-100 | 10 | 10 | $1.2 \times 10^{-4}$ |
| 2 | pAG-100 | 0.1 | 10 | $1.6 \times 10^{-5}$ |
| 3 | pAG-100 | 1 | 3 | $3.4 \times 10^{-4}$ |
| 3 | pAG-101, linearized with BamHI | 20 | 0.05 | $1.1 \times 10^{-5}$ |

5. Results of Transformation with lacZ Plasmids

In order to investigate the functioning ability of the TEF promoter further, derivatives of the plasmid pAG-100 in which the gene for β-galactosidase from *E. coli* (lacZ gene) is under the control of the TEF promoter were constructed. For this, various regions of the promoter region of the TEF gene were fused in front of the open reading frame of the lacZ gene, with the first seven codons of the lacZ gene being replaced by the first eight codons of the TEF gene. The plasmid pAG-110 harbors an approximately 1.5 kb-long HincII TEF promoter fragment in front of the lacZ gene and the plasmid pAG-111 the 403 bp-long HindIII/HincII TEF promoter fragment which has already been employed for the constructions of pAG-100 and pAG-101. The plasmid pAG-112 harbors a 294 bp-long TEF promoter fragment, plasmid pAG-113 a 239 bp-long TEF promoter fragment and pAG-114 a 158 bp-long TEF promoter fragment.

In addition, pAG-115 which harbors the open reading frame of the lacZ gene without fusion to a promoter fragment was constructed as control plasmid.

After transformation of these plasmids into *A. gossypii*, the expression of the lacZ gene was checked using a color test. The β-galactosidase encoded by the lacZ gene cleaves X-Gal (5-bromo-4-chloro-3-indoyl β-D-galactoside) to the blue dye 5-bromo-4-chloroindigo. pAG-110, pAG-111 and pAG-112 transformants formed blue colonies on medium which contains X-Gal (Miller, Experiments in Molecular Genetics, Cold Spring Harbor, N.Y. 1972, 48) in a concentration of 100 µg/ml. No blue coloration was visible in the case of transformants which contained pAG-113, pAG-114 or pAG-115.

FIG. 16 shows a summary of the various TEF promoter fragments which were fused in front of the lacZ gene. A + represents a blue coloration of the colonies on X-Gal-containing medium, a − represents no visible blue coloration.

For a further investigation of β-galactosidase expression, the β-galactosidase activity of liquid cultures of pAG-110, pAG-111, pAG-112, pAG-113, PAG-114 and pAG-115 transformants was determined. The mycelium was disrupted with glass beads for this (Rose, M.; Casadaban, M. J. and Botstein, D., Proc. Natl. Acad. Sci. U.S.A. Vol. 78, No. 4 (1981), 2460–2464). 0.5 g of mycelium which had grown in MA2 liquid medium containing 200 µg/ml G 418 was taken up in 0.1 mM Tris, pH 8.0/20% (vol/vol) glycerol/1 mM DTT/1 mM PMSF and, after addition of 0.5 g of glass beads (diameter 0.45–0.5 mm), frozen away at −20° C. To disrupt the mycelium it was shaken vigorously (Vortex) at 4° C. for 15 sec. 12 times. It was subsequently centrifuged at 10000 rpm (Sorvall cooled centrifuge) twice for 20 min. The supernatants were diluted 1:10 and 1:20, respectively, in Z buffer (0.06M $Na_2HPO_4$/0.04M $NaH_2PO_4$/0.01M KCl/ 0.001M $MgSO_4$/0.05M β-mercaptoethanol). The β-galactosidase activity in the diluted protein crude extracts was determined by cleavage of o-nitrophenyl β-D-galactopyranoside (Miller, Experiments in Molecular Genetics, Cold Spring Harbor, N.Y. 1972, 353 ff). The enzyme activity was related to the protein concentration in the crude extract, which was determined by the Bradford method (Bradford, M. M., Anal. Biochem. 72 (1976), 248–254). The results of the β-galactosidase activity determination are shown in Table 2. The amount of o-nitrophenol (measured as $OD_{420}$) liberated per minute and mg of total protein is indicated.

TABLE 2

| | β-Galactosidase expression | |
|---|---|---|
| Plasmid | Measurement No. | β-Galactosidase activity (relative units, $OD_{420}$/mg min.) |
| pAG-110 | 1 | 3.62 |
| | 2 | 3.54 |
| | 3 | 2.45 |
| pAG-111 | 1 | 3.07 |
| | 2 | 3.29 |
| | 3 | 3.63 |
| | 4 | 3.16 |
| pAG-112 | 1 | 1.89 |
| | 2 | 1.90 |
| | 3 | 1.79 |
| | 4 | 1.75 |
| pAG-113 | 1 | 0 |
| | 2 | 0 |
| pAG-114 | 1 | 0 |
| | 2 | 0 |
| pAG-115 | 1 | 0 |
| | 2 | 0 |

We claim:

1. An isolated promoter of the translation elongation factor EF-1α gene of *Ashbya gossypii* comprising the nucleotide sequence as set forth in SEQ ID NO:1.

2. A genetically modified fungus into which the isolated promoter of claim 1 has been inserted.

3. The genetically modified fungus of claim 2, wherein said fungus is *Ashbya gossypii*.

4. A method for producing protein which comprises culturing the fungus of claim 2 in a suitable nutrient medium and isolating said protein.

5. The method of claim 4, wherein said fungus is *Ashbya gossypii*.

6. An isolated terminator of the translation elongation factor EF-1α gene of *Ashbya gossypii* comprising the sequence of nucleotides 1513–2095 of SEQ ID NO:2.

7. The method of claim 4, wherein said protein is β-galactosidase.

8. The method of claim 7, wherein said fungus is *Ashbya gossypii*.

\* \* \* \* \*

SEQUENCE LISTING ( 1 ) GENERAL INFORMATION:

( i i i ) NUMBER OF SEQUENCES: 16

( 2 ) INFORMATION FOR SEQ ID NO: 1:

( i ) SEQUENCE CHARACTERISTICS:
        ( A ) LENGTH: 409 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 1:

```
AAGCTTGCCT    CGTCCCNCGC    GGGTCACCCG    GCCAGCGACA    TGGAGGCCCA    GATACCCTCC  60
TTGACAGTCT    TGACGTGCGC    AGCTCACGGG    GCATGATGTG    ACTGTCGCCC    GTACATTTA  120
CCCATACATC    CCCATGTATA    ATCATTTGCA    TCCATACATT    TTGATGGCCG    CGACGGCGC  180
AAGCAAAAAT    TACGGCTCCT    CGCTGCAGAC    CTGCGAGCAG    GGAAACGCTC    CCCTCAGCA  240
ACGCGTTGAA    TTCTCCCCAC    GGCGCGCCCC    TGTAGAGAAA    TATAAAGGT     TAGGATTTG  300
CACTGAGGTT    CTTCTTTCAT    ATACTTCCTT    TTAAAATCTT    GCTAGGATAC    AGTTCTCAC  360
TCACATCCGA    ACATAAACAA    AAATGGGTAA    GGAAAAGACT    CACGTTAAC                409
```

( 2 ) INFORMATION FOR SEQ ID NO:2:

( i ) SEQUENCE CHARACTERISTICS:
        ( A ) LENGTH: 2095 base pairs
        ( B ) TYPE: nucleic acid
        ( C ) STRANDEDNESS: single
        ( D ) TOPOLOGY: linear (i i) MOLECULE TYPE: genomic DNA (x i) SEQUENCE DESCRIPTION: SEQ ID NO: 2:

| | | | | | |
|---|---|---|---|---|---|
| GAATTCTCCC | CACGGCGCGC | CCCTGTAGAG | AAATATAAAA | GGTTAGGATT | TGCCACTGAG 60 |
| GTTCTTCTTT | CATATACTTC | CTTTTAAAAT | CTTGCTAGGA | TACAGTTCTC | ACATCACAT 120 |
| CGAACATAAA | CAAAAATGGG | TAAGGAAAAG | ACTCACGTTA | ACGTTGTCGT | CATCGGTCA 180 |
| GTCGACTCTG | GTAAGTCTAC | TACCACCGGT | CACTTGATCT | ACAAGTGTGG | TGGTATTGA 240 |
| AAGAGAACCA | TCGAGAAGTT | CGAGAAGGAG | GCTGCCGAGT | TGGGTAAGGG | TTCTTTCAA 300 |
| TACGCCTGGG | TTTTGGACAA | ATTGAAGGCT | GAGAGAGAGA | GAGGTATCAC | CATCGACAT 360 |
| GCGTTGTGGA | AGTTCGAGAC | TCCAAAGTAC | CACGTCACTG | TCATTGACGC | CCCAGGCCA 420 |
| AGAGACTTCA | TCAAGAACAT | GATTACCGGT | ACTTCTCAAG | CTGACTGTGC | CATCTTGAT 480 |
| ATTGCTGGTG | GTGTCGGTGA | GTTCGAGGCT | GGTATCTCCA | AGGACGGTCA | GACCAGAGA 540 |
| CACGCTTTGT | TGGCTTACAC | CTTGGGTGTC | AAGCAGTTGA | TCGTTGCCAT | CAACAAGAT 600 |
| GACTCCGTCA | AGTGGGACGA | GTCCAGATAC | CAGGAGATTG | TCAAGGAGAC | CTCCAACTT 660 |
| ATCAAGAAGG | TCGGTTACAA | CCCTAAGACT | GTTCCATTCG | TTCCAATCTC | CGGCTGGAA 720 |
| GGTGACAACA | TGATTGAGGC | CACCACCAAC | GCCCATGGT | ACAAGGGCTG | GGAGAAGGA 780 |
| ACCAAGGCTG | GTGCCGTCAA | GGGTAAGACC | TTGTTGGAGG | CCATTGACGC | CATTGAGCC 840 |
| CCTGTCAGAC | CAACTGACAA | GGCATTGAGA | TTGCCATTGC | AGGATGTCTA | CAAGATCGG 900 |
| GGTATTGGTA | CGGTTCCAGT | CGGCAGAGTC | GAGACCGGTG | TCATCAAGCC | AGGTATGGT 960 |
| GTTACCTTCG | CCCCATCCGG | TGTCACCACT | GAAGTCAAGT | CCGTCGAGAT | GCACCACG 1020 |
| CAATTGGAGG | AGGGTGTCCC | AGGTGACAAC | GTTGGTTTCA | ACGTCAAGAA | CGTCTCCG 1080 |
| AAGGAGATCA | GAAGAGGTAA | CGTTTGCGGT | GACTCCAAGA | ACGACCCACC | AAAGGCTG 1140 |
| GAGTCCTTCA | ACGCTACCGT | CATTGTCTTG | AACCACCCAG | GTCAAATCTC | TGCCGGTT 1200 |
| TCTCCAGTCT | TGGACTGTCA | CACTGCCCAC | ATTGCTTGTA | AGTTCGACGA | GTTGTTGG 1260 |
| AAGAACGACA | GAAGAACCGG | TAAGAAGTTG | GAAGACTCTC | CAAAGTTCCT | AAAGGCCG 1320 |
| GACGCTGCCA | TGGTCAAGTT | TGTCCCATCC | AAGCCAATGT | GTGTTGAGGC | TTTCACCG 1380 |
| TACCCACCAT | TGGGTAGATT | CGCTGTCAGA | GACATGAGAC | AGACCGTTGC | TGTCGGTG 1440 |
| ATCAAGTCTG | TTGTCAAGTC | CGACAAGGCT | GGTAAGGTCA | CCAAGGCCGC | CCAAAAGG 1500 |
| GGTAAGAAAT | AGAGTAACTG | ACAATAAAAA | GATTCTTGTT | TTCAAGAACT | TGTCATTT 1560 |
| ATAGTTTTTT | TATATTGTAG | TTGTTCTATT | TTAATCAAAT | GTTAGCGTGA | TTTATATT 1620 |
| TTTTGCCTCG | ACATCATCTG | CCCAGATGCG | AAGTTAAGTG | CGCAGAAAGT | AATATCAT 1680 |
| GTCAATCGTA | TGTGAATGCT | GGTCGCTATA | CTGCTGTCGA | TTCGATACTA | ACGCCGCC 1740 |
| CCAGTGTCTA | CCTGTCAAAT | TTGCCAGCGT | CAAATGCCTC | CAGGATAGAA | TATGCTCG 1800 |
| AACTGTTGAA | GTCCATCAAC | AAGGATAACC | CATATGCTCT | ATCGGCGGAG | AAAACGTT 1860 |
| CAGAGCCGCT | TCCTTCCGCA | GACGTGCCCC | TTCCACTGCT | AGATGAGAAG | TACGGGGT 1920 |
| TTAGTGTTTC | CAGGCCTCGT | AAATGCCGCA | ATAAATGCTT | CCTTGGGTTC | GCTACGCC 1980 |
| CTCAGGCAGA | CGAGTTTCTA | CAAAACTTCA | AGGACCGCCT | TTTCATATAT | GGCCACCA 2040 |
| TCAATATAGA | GCCAGCGAAC | GATGATGCAT | TCTGGTATAT | TGAACGCGAG | GATCC 2095 |

(2) INFORMATION FOR SEQ ID NO:3:

(i) SEQUENCE CHARACTERISTICS:
(A) LENGTH: 2115 base pairs
(B) TYPE: nucleic acid ( C ) STRANDEDNESS: single
( D ) TOPOLOGY: linear ( i i ) MOLECULE TYPE: genomic DNA ( x i ) SEQUENCE DESCRIPTION: SEQ ID NO: 3:

| | | | | | |
|---|---|---|---|---|---|
| GTCGACTGTA | ATCCGGGCAG | CGCAACGGAA | CATTCATCAG | TGTAAAAATG | GAATCAATAA 60 |
| AGCCCTGCGC | AGCGCGCAGG | GTCAGCCTGA | ATACGCGTTT | AATGACCAGC | ACAGTCGTG 120 |
| TGGCAAGGTC | AGAATAGCGC | TGAGGTCTGC | CTCGTGAAGA | AGGTGTTGCT | GACTCATAC 180 |
| AGGCCTGAAT | CGCCCCATCA | TCCAGCCAGA | AAGTGAGGGA | GCCACGGTTG | ATGAGAGCT 240 |
| TGTTGTAGGT | GGACCAGTTG | GTGATTTTGA | ACTTTGCTT | TGCCACGGAA | CGGTCTGCG 300 |
| TGTCGGGAAG | ATGCGTGATC | TGATCCTTCA | ACTCAGCAAA | AGTTCGATTT | ATTCAACAA 360 |
| GCCACGTTGT | GTCTCAAAAT | CTCTGATGTT | ACATTGCACA | AGATAAAAAT | ATATCATCA 420 |
| GAACAATAAA | ACTGTCTGCT | TACATAAACA | GTAATACAAG | GGGTGTTATG | AGCCATATT 480 |
| AACGGGAAAC | GTCTTGCTCG | AAGCTTGCCT | CGTCCCACGC | GGGTCACCCG | GCCAGCGAC 540 |
| TGGAGGCCCA | GATACCCTCC | TTGACAGTCT | TGACGTGCGC | AGCTCACGGG | GCATGATGT 600 |
| ACTGTCGCCC | GTACATTTAG | CCCATACATC | CCCATGTATA | ATCATTTGCA | TCCATACAT 660 |
| TTGATGGCCG | CGACGGCGCG | AAGCAAAAT | TACGGCTCCT | CGCTGCAGAC | CTGCGAGCA 720 |
| GGAAACGCTC | CCCTCAGCAG | ACGCGTTGAA | TTCTCCCCAC | GGCGCGCCCC | TGTAGAGAA 780 |
| TATAAAGGT | TAGGATTTGC | CACTGAGGTT | CTTCTTTCAT | ATACTTCCTT | TTAAAATCT 840 |
| GCTAGGATAC | AGTTCTCACA | TCACATCCGA | ACATAAACAA | AAATGGGTAA | GGAAAAGAC 900 |
| CACGTTTCGA | GGCCGCGATT | AAATTCCAAC | ATGGATGCTG | ATTTATATGG | GTATAAATG 960 |
| GCTCGCGATA | ATGTCGGGCA | ATCAGGTGCG | ACAATCTATC | GATTGTATGG | GAAGCCCG 1020 |
| GCGCCAGAGT | TGTTTCTGAA | ACATGGCAAA | GGTAGCGTTG | CCAATGATGT | TACAGATG 1080 |
| ATGGTCAGAC | TAAACTGGCT | GACGGAATTT | ATGCCTCTTC | CGACCATCAA | GCATTTTA 1140 |
| CGTACTCCTG | ATGATGCATG | GTTACTCACC | ACTGCGATCC | CCGGGAAAAC | AGCATTCC 1200 |
| GTATTAGAAG | AATATCCTGA | TTCAGGTGAA | AATATTGTTG | ATGCGCTGGC | AGTGTTCC 1260 |
| CGCCGGTTGC | ATTCGATTCC | TGTTTGTAAT | TGTCCTTTTA | ACAGCGATCG | CGTATTTC 1320 |
| CTCGCTCAGG | CGCAATCACG | AATGAATAAC | GGTTTGGTTG | ATGCGAGTGA | TTTTGATG 1380 |
| GAGCGTAATG | GCTGGCCTGT | TGAACAAGTC | TGGAAAGAAA | TGCATAAGCT | TTTGCCAT 1440 |
| TCACCGGATT | CAGTCGTCAC | TCATGGTGAT | TTCTCACTTG | ATAACCTTAT | TTTTGACG 1500 |
| GGGAAATTAA | TAGGTTGTAT | TGATGTTGGA | CGAGTCGGAA | TCGCAGACCG | ATACCAGG 1560 |
| CTTGCCATCC | TATGGAACTG | CCTCGGTGAG | TTTTCTCCTT | CATTACAGAA | ACGGCTTT 1620 |
| CAAAAATATG | GTATTGATAA | TCCTGATATG | AATAAATTGC | AGTTTCATTT | GATGCTCG 1680 |
| GAGTTTTTCT | AATCAGAATT | GGTTAATTGG | TTGTAACACT | GGCAGAGCAT | TACGCTGA 1740 |
| TGACGGGACG | GCGGCTTTGT | TGAATAAATC | GAACTTTTGC | TGAGTTGAAG | GATCAGAT 1800 |
| CGCATCTTCC | CGACAACGCA | GACCGTTCCG | TGGCAAAGCA | AAAGTTCAAA | ATCACCAA 1860 |
| GGTCCACCTA | CAACAAAGCT | CTCATCAACC | GTGGCTCCCT | CACTTTCTGG | CTGGATGA 1920 |
| GGGCGATTCA | GGCCTGGTAT | GAGTCAGCAA | CACCTTCTTC | ACGAGGCAGA | CCTCAGCG 1980 |
| ATTCTGACCT | TGCCATCACG | ACTGTGCTGG | TCATTAAACG | CGTATTCAGG | CTGACCCT 2040 |
| GCGCTGCGCA | GGGCTTTATT | GATTCCATTT | TTACACTGAT | GAATGTTCCG | TTGCGCTG 2100 |
| CGGATTACAG | TCGAC | | | | 2115 |

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 4:

CGAACATAAA CAAAAATGGG TAAGGAAAAG        30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 5:

CTTTTCCTTA CCCATTTTG TTTATGTTCG        30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 6:

CGAACATAAA CAACCATGGG TAAGGAAAAG        30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 7:

CTTTTCCTTA CCCATGGTTG TTTATGTTCG        30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 8:

CGAACATAAA CAAAAATGCA TAAGGAAAAG        30

( 2 ) INFORMATION FOR SEQ ID NO:9:

( i ) SEQUENCE CHARACTERISTICS:
        ( A ) LENGTH: 30 base pairs
        ( B ) TYPE: nucleic acid ( C ) STRANDEDNESS: single
        ( D ) TOPOLOGY: linear ( i i ) MOLECULE TYPE: genomic DNA ( x i ) SEQUENCE DESCRIPTION: SEQ ID NO: 9:

CTTTTCCTTA TGCATTTTTG TTTATGTTCG                                                30

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 10:

CGAACATAAA CAAGCATGCG TAAGGAAAAG                                                30

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 11:

CTTTTCCTTA CGCATGCTTG TTTATGTTCG                                                30

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 12:

GGCTGGTAAG AAATAGAGTA ACTGACAAT                                                 29

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 13:

ATTGTCAGTT ACTCTATTTC TTACCAGCC                                                 29

( 2 ) INFORMATION FOR SEQ ID NO:14:

( i ) SEQUENCE CHARACTERISTICS:
        ( A ) LENGTH: 681 base pairs
        ( B ) TYPE: nucleic acid
        ( C ) STRANDEDNESS: single
        ( D ) TOPOLOGY: linear ( i i ) MOLECULE TYPE: genomic DNA (x i) SEQUENCE DESCRIPTION: SEQ ID NO: 14:

```
AAGCTTGCCT CGTCCCCGCC GCGGGTCACC CGGCCAGCGA CATGGAGGCC CAGATACCCT      60
CCTTGACAGT CTTGACGTGC GCAGCTCACG GGGCATGATG TGACTGTCGC CCGTACATTT     120
AGCCCATACA TCCCATGTA  TAATCATTTG CATCCATACA TTTGATGGC  CGCGACGGCG     180
CGAAGCAAAA ATAACGGCTC CTCGCTGCAG ACCTGCGAGC AGGGAAACGC TCCCCTCAGC     240
AGACGCGTTG AATTCTCCCC ACGGCGCGCC CCTGTAGAGA AATATAAAAG GTTAGGATTT     300
GCCACTGAGG TTCTTCTTTC ATATACTTCC TTTTAAAATC TTGCTAGGAT ACAGTTCTCA     360
CATCACATCC GAACATAAAC AAAAATGGGT AAGGAAAGA  CTCACGTTGA CCTGGAGGTC     420
CCGCCCAAAA GGCTGGTAAG AAATAGAGTA CTGACAATAA AAAGATTCTT GTTTCAAGA     480
ACTTGTCATT TGTATAGTTT TTTTATATTG TAGTTGTTCT ATTTAATCA  ATGTTAGCGT     540
GATTTATATT TTTTTGCCT  CGACATCATC TGCCCAGATG CGAAGTTAAG TGCGCAGAAA     600
GTAATATCAT GCGTCAATCG TATGTGAATG CTGGTCGCTA TACTGCTGTC GATTCGATAC     660
TAACGCCGCC ATCCAGTGTC T                                              681
```

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: genomic DNA (x i) SEQUENCE DESCRIPTION: SEQ ID NO: 15:

```
GGCTGGTAAG AAATAGAGT                                                  19
```

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: genomic DNA (x i) SEQUENCE DESCRIPTION: SEQ ID NO: 16:

```
CCGACCATTC TTTATCTCA                                                  19
```